United States Patent [19]

Phillips et al.

[11] Patent Number: 5,652,258
[45] Date of Patent: Jul. 29, 1997

[54] 2-(4-IMIDAZOYL) CYCLOPROPYL DERIVATIVES

[75] Inventors: James G. Phillips, Bay Village; Clark E. Tedford, South Russell; Amin Mohammed Khan, Solon; Stephen L. Yates, Aurora, all of Ohio

[73] Assignee: Gliatech, Inc., Cleveland, Ohio

[21] Appl. No.: 453,359

[22] Filed: May 30, 1995

[51] Int. Cl.$^6$ ............... A61K 31/415; C07D 233/64; C07D 233/56
[52] U.S. Cl. .............. 514/400; 548/338.1; 548/340.1; 548/341.1; 548/341.5; 548/342.1; 548/345.1
[58] Field of Search ............... 548/338.1, 340.1, 548/341.1, 341.5, 342.1, 345.1; 514/400

[56] References Cited

U.S. PATENT DOCUMENTS 4,707,487  11/1987  Arrang et al.
5,217,986   6/1993  Pomponi et al.
5,290,790   3/1994  Arrang et al.

FOREIGN PATENT DOCUMENTS

WO92/15567  9/1992  WIPO.
WO93/14070  6/1993  WIPO.

OTHER PUBLICATIONS

Archiv der Parmazie (D 1358 E) *Archiv der Pharmazie*, (1973) Band 306: 933–940.
Burger, et al., *J. Med. Chem.* (1970), 13: 33–35.
Zervas et al., *J. Am. Chem. Soc.*, 78: 1359 (1956).
West et al., (1990) *Mol. Pharmacol.* 3.8 610–613.
(Schwartz, 1975) *Life Sci.* 1.7: 503–518.
(Inagaki et al., 1988) *J. Comp. Neurol.* 273: 283–300.
(Schwartz et al., 1986) *TIPS* 8: 24–28.
(Arrang et al., 1983) *Nature* 302: 832–837.
(Lin et al., 1990) *Brain Res.* 529: 325–330.
S.M. Berge, et al., "Pharmaceutical Sales," *J. Pharm. Sci.*, 6,6: 1–19 (1977).

*Primary Examiner*—Patricia L. Morris
*Attorney, Agent, or Firm*—Dressler, Rockey, Milnamow & Katz, Ltd.

[57] ABSTRACT

The present invention provides compounds having $H_3$ histamine receptor antagonist activity of the general formula:

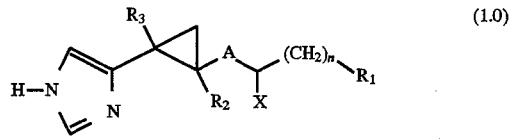

(1.0)

where

X is H, A is —$CH_2CH_2$—, —$COCH_2$—, —CONH—, —CON($CH_3$)—, —CH=CH—, —C≡C—, —$CH_2$—NH—, —$CH_2$—$NCH_3$—, —CH(OH)$CH_2$—, —NH—$CH_2$—, —N($CH_3$)—$CH_2$—, —$NHSO_2$—, —$CH_2$O—, —$CH_2$S—, $CH_2SO_2$—, or —$CH_2$S(O)—;

$R_2$ is a hydrogen or a methyl or ethyl group;

$R_3$ is a hydrogen or a methyl or ethyl group;

n is 0, 1, 2, 3, 4, 5, or 6; and $R_1$ is selected from the group consisting of (a) $C_3$ to $C_8$ cycloalkyl; (b) H; (c) phenyl or substituted phenyl; (d) alkyl; (e) heterocyclic; and (f) bicyclic alkyl; and when X is $NH_2$, $NHCH_3$, $N(CH_3)_2$, OH, $OCH_3$, $NHR_4$, $OR_4$, SH, $SR_4$, or $SO_2R_4$; A is —NHCO—, —N($CH_3$)—CO—, —$NHCH_2$—, —N($CH_3$)—$CH_2$—, —$NHSO_2$—, —CH=CH—, —CH=CHF—, —$COCH_2$—, —$CH_2CH_2$—, —CH(OH)$CH_2$—, or —C≡C—;

$R_2$ is a hydrogen or a methyl or ethyl group;

$R_3$ is a hydrogen or a methyl or ethyl group;

n is 0, 1, 2, 3, 4, 5, or 6;

$R_1$ is selected from the group consisting of (a) $C_3$ to $C_8$ cycloalkyl; (b) H; (c) phenyl or substituted phenyl; (d) alkyl; (e) heterocyclic; and (f) bicyclic alkyl and $R_4$ is designated to mean that X is contained within a ring such as octahydroindole.

4 Claims, No Drawings

2-(4-IMIDAZOYL) CYCLOPROPYL DERIVATIVES

TECHNICAL FIELD

This invention relates to compounds having pharmacological activity, to compositions containing these compounds, and to a method of treatment employing the compounds and compositions. More particularly, this invention concerns certain 2-(4-imidazoyl) cyclopropyl derivatives and their salts or solvates. These compounds have $H_3$ histamine receptor antagonist activity. This invention also relates to pharmaceutical compositions containing these compounds, and to a method of treating disorders in which histamine $H_3$ receptor blockade is beneficial.

BACKGROUND OF THE INVENTION

Histamine is a chemical messenger involved in various complex biological actions. When released, histamine interacts with specific macromolecular receptors on the cell surface or within a target cell to elicit changes in many different bodily functions. Various cell types including smooth muscle, blood cells, cells of the immune system, endocrine and exocrine cells as well as neurons respond to histamine by stimulating the formation of intracellular signals, including formation of phosphatidylinositol or adenylate cyclase. Evidence that histamine plays a role as a neurotransmitter was established by the mid to late 1970's (Schwartz, 1975) *Life Sci.* 17: 503–518. Immunohistochemical studies identified histaminergic cell bodies in the tuberomammillary nucleus of the posterior hypothalamus with widespread projections in the dicencephalon and telencephalon (Inagaki et al., 1988) *J. Comp. Neurol.* 273: 283–300.

Identification of two histamine receptors ($H_1$ and $H_2$) was reported to mediate the biochemical actions of histamine on neurons. Recently, studies have demonstrated the existence of a third subtype of histamine receptor, the histamine $H_3$ receptor (Schwartz et al., 1986) *TIPS* 8: 24–28. Various studies have now demonstrated that histamine $H_3$ receptors are found on the histaminergic nerve terminals in the brains of several species, including man (Arrang et al., 1983) *Nature* 302: 832–837. The $H_3$ receptor found on the histaminergic nerve terminal was defined as an autoreceptor and could intimately control the amount of histamine released from the neurons. Histamine, the natural compound, was capable of stimulating this autoreceptor but when tested against known $H_1$ and $H_2$ receptor agonists and antagonists, a distinct pharmacological profile emerged. Further, $H_3$ receptors have been identified on cholinergic, serotoninergic and monoamine nerve terminals in the peripheral nervous system (PNS) and central nervous system including the cerebral codex and cerebral vessels. These observations suggest that $H_3$ receptors are uniquely located to modulate histamine as well as other neurotransmitter release, and $H_3$ antagonists could be important mediators of neuronal activity.

As stated, CNS histaminergic cell bodies are found in the magnocellular nuclei of the hypothalamic mammillary region and these neurons project diffusely to large areas of the forebrain. The presence of histaminergic cell bodies in the tuberomamillary nucleus of the posterior hypothalamus, a brain area involved in the maintenance of wakefulness, and their projections to the cerebral cortex suggest a role in modulating the arousal state or sleep-wake. The histaminergic projection to many limbic structures such as the hippocampal formation and the amygdaloid complex suggest roles in functions such as autonomic regulation, control of emotions and motivated behaviors, and memory processes.

The concept that histamine is important for the state of arousal, as suggested by the location of histaminergic pathways, is supported by other types of evidence. Lesions of the posterior hypothalamus is well known to produce sleep. Neurochemical and electrophysiological studies have also indicated that the activity of histaminergic neurons is maximal during periods of wakefulness and is suppressed by barbiturates and other hypnotics. Intraventricular histamine induces the appearances of an arousal EEG pattern in rabbits and increased spontaneous locomotor activity, grooming and exploratory behavior in both saline and pentobarbital-treated rats.

In contrast, a highly selective inhibitor of histidine decarboxylase, the sole enzyme responsible for histamine synthesis, has been shown to impair waking in rats. These data support the hypothesis that histamine may function in modulating behavioral arousal. The role of the $H_3$ receptor in sleep-waking parameters has been recently demonstrated (Lin et al., 1990) *Brain Res.* 529: 325–330. Oral administration of RAMHA, a $H_3$ agonist, caused a significant increase in deep slow wave sleep in the cat. Conversely, thioperamide, a $H_3$ antagonist, enhanced wakefulness in a dose-dependent fashion. Thioperamide has also been shown to increase wakefulness and decrease slow wave and REM sleep in rats. These findings are consistent with in vivo studies demonstrating that thioperamide caused an increase in synthesis and release of histamine. Together, these data demonstrate that selective $H_3$ antagonists may be useful in the treatment of arousal states and sleep disorders.

Serotonin, histamine, and acetylcholine have all been demonstrated to be diminished in the Alzheimer's (AD) brain. The histamine $H_3$ receptor has been demonstrated to regulate the release of each of these neurotransmitters. An $H_3$ receptor antagonist would therefore be expected to increase the release of these neurotransmitters in brain. Since histamine has been demonstrated to be important in arousal and vigilance, $H_3$ receptor antagonists might enhance arousal and vigilance via increasing levels of neurotransmitter release and improve cognition. Thus, the use of $H_3$ receptor antagonists in AD, attention deficit disorders (ADD), age-related memory dysfunction and other cognitive disorders would be supported.

$H_3$ receptor antagonists may be useful in treating several other CNS disorders. It has been suggested that histamine may be involved in the control of sleep/wake states as well as states of arousal and alertness, cerebral circulation, energy metabolism, and hypothalmic hormone secretion. Recent evidence has indicated the possible use of $H_3$ antagonists in the treatment of epilepsy. Work has demonstrated an inverse correlation between the duration of clonic convulsions and brain histamine levels. Thioperamide, a $H_3$ antagonist, was also shown to significantly and dose-dependently decrease the durations of every convulsive phase after electrically-induced convulsions and increase the electroconvulsive threshold.

In spite of their low density, $H_3$ receptor binding sites can be detected outside the brain. Several studies have revealed the presence of $H_3$ heteroreceptors in the gastrointestinal tract, as well as upon neurons of the respiratory tract. Accordingly, an $H_3$ receptor antagonist may be useful in the treatment of diseases and conditions such as asthma, rhinitis, airway congestion, inflammation, hyper and hypo motility and acid secretion of the gastrointestinal tract. Peripheral or central blockade of $H_3$ receptors may also contribute to changes in blood pressure, heart rate and cardiovascular output and could be used in the treatment of cardiovascular diseases.

U.S. Pat No. 4,707,487 discloses compounds of the general formula:

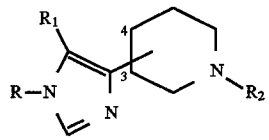

in which $R_1$ denotes H, $CH_3$, or $C_2H_5$, R denotes H or $R_2$ and $R_2$ denotes an alkyl, piperonyl, 3-(1-benzimidazolonyl)-propyl group; a group of formula:

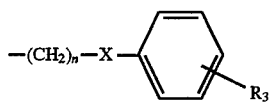

in which n is 0, 1, 2, or 3, X is a single bond or alternatively —O—, —S—, —NH—, —CO—, —CH=CH— or

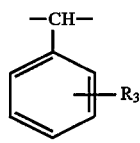

and $R_3$ is H, $CH_3$, F, CN or an acyl group; or alternatively a group of formula:

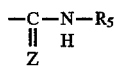

in which Z denotes an O or S atom or a divalent group NH, N—$CH_3$, or N—CN, and $R_5$ denotes an alkyl group, a cycloalkyl group which can bear a phenyl substituent, a phenyl group which can bear a $CH_3$ or F substituent, a phenylalkyl ($C_1$-$C_3$) group or a naphthyl, adamantyl, or p-toluenesulphonylgroup. It is also disclosed that these compounds antagonize the histamine $H_3$ receptors and increase the rate of renewal of cerebral histamine.

WO 92/15567 discloses compounds of general formula:

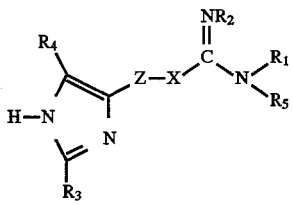

wherein: Z is a group of formula $(CH_2)_m$, wherein m=1–5 or a group of the formula:

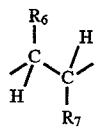

wherein $R_6$=($C_1$-$C_3$) alkyl, $R_7$=($C_1$-$C_3$) alkyl; X represents S, NH, or $CH_2$; $R_1$ represents hydrogen, ($C_1$-$C_3$) alkyl-, aryl ($C_1$-$C_{10}$) alkyl-, wherein aryl may optionally be substituted, aryl, ($C_5$-$C_7$) cycloalkyl, ($C_1$-$C_{10}$) alkyl-, or a group of the formula:

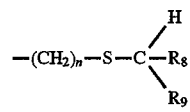

wherein n=1–4, $R_8$ is aryl, aryl ($C_1$-$C_{10}$) alkyl-, ($C_5$-$C_7$) cycloalkyl- or ($C_5$-$C_7$) cycloalkyl ($C_1$-$C_{10}$) alkyl-, and $R_9$ is hydrogen, ($C_1$-$C_{10}$) alkyl- or aryl; $R_2$ and $R_5$ represent hydrogen, ($C_1$-$C_3$) alkyl-, aryl or arylalkyl-, wherein aryl may optionally be substituted; $R_3$ represents hydrogen, ($C_1$-$C_3$) alkyl, aryl, or arylalkyl-, wherein aryl may be substituted; and $R_4$ represents hydrogen, amino-, nitro-, cyano-, halogen-, ($C_1$-$C_3$) alkyl, aryl, or arylalkyl-, wherein aryl may optionally be substituted; wherein aryl is phenyl, substituted phenyl, naphthyl, substituted naphthyl, pyridyl or substituted pyridyl. These compounds are reported to have agonistic or antagonistic activity on the histamine $H_3$ receptor.

U.S. Pat. No. 5,217,986 discloses compound of formula:

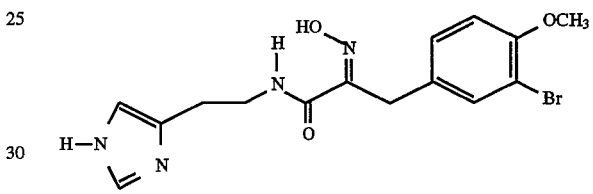

This compound is reported to be active in an $H_3$ receptor assay, is reported to be an $H_3$ antagonist on guinea pig ileum, and accordingly is said to be useful in the treatment of diseases and conditions such as asthma, rhinitis, airway congestion, inflammation, cardiac arrhythmias, hypertension, hyper and hypo motility and acid secretion of the gastrointestinal tract, hypo and hyper-activity of the central nervous system, migraine, and glaucoma.

WO 93/14070 discloses compounds of general formula:

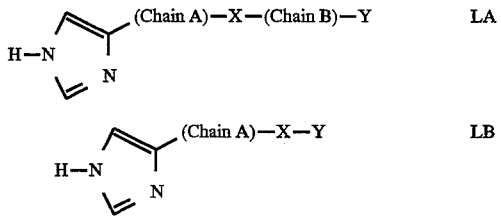

Chain A represents a hydrocarbon chain, saturated or unsaturated, of 1–6 carbon atoms in length; X represents —O—, —S—, —NH—, —NHCO—, —N(alkyl)CO—, —NHCONH—, —NH—CS—NH—, —NHCS—,—O—CO—, —CO—O—, —OCONH—, —OCON(alkyl)—, —OCONH—CO—, —CONH—, —CON(alkyl)—, —SO—, —CO—, —CHOH—, —NR—C(=NR")—NR'—, R and R' can be hydrogen or alkyl and R" is hydrogen or cyano, or $COY_1$, $Y_1$ is alkoxy radical. Chain B represents an alkyl group —$(CH_2)_n$—, n=0–5 or an alkyl-chain of 2–8 carbon atoms interrupted by an oxygen or sulfur atom or a group like —$(CH_2)_n$—O— or —$(CH_2)_n$—S— wherein n=1 or 2. Y represents ($C_1$-$C_8$)alkyl, ($C_3$-$C_6$) cycloalkyl, bicycloalkyl, aryl, cycloalkenyl, heterocycle.

U.S. Pat. No. 5,290,790 discloses compounds of the same general structure as U.S. Pat. No. 4,707,487:

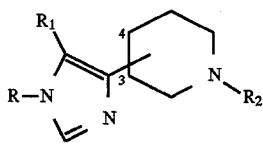

but specifically includes amides wherein $R_2$ is CO—NR'R" and R'R" are independently selected from the group consisting of (a) hydrogen; (b) phenyl or substituted phenyl; (c) alkyl; (d) cycloalkyl; and (e) alkylcycloalkyl such as cyclohexylmethyl or cyclopentylethyl.

SUMMARY OF THE INVENTION

The present invention provides, in its principal aspect, compounds of the general formula:

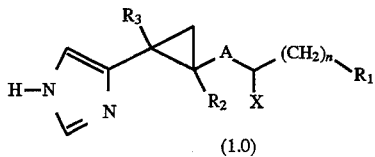

where
when X is H, A is —CH$_2$CH$_2$—, —COCH$_2$—, —CONH—, —CONCH$_3$)—, —CH=CH—, —C≡C—, —CH$_2$—NH—, —CH$_2$—N(CH$_3$)—, —CH(OH)CH$_2$—, —NH—CH$_2$—, —N(CH$_3$)—CH$_2$—, —NHSO$_2$—, —CH$_2$O—, —CH$_2$S—, CH$_2$SO$_2$—, or —CH$_2$S(O)—;

$R_2$ is a hydrogen or a methyl or ethyl group;

$R_3$ is a hydrogen or a methyl or ethyl group;

n is 0, 1, 2, 3, 4, 5, or 6; and $R_1$ is selected from the group consisting of (a) $C_3$ to $C_8$ cycloalkyl; (b) H; (c) phenyl or substituted phenyl; (d) alkyl; (e) heterocyclic; and (f) bicyclic alkyl; and when X is NH$_2$, NHCH$_3$, N(CH$_3$)$_2$, OH, OCH$_3$, NHR$_4$, OR$_4$, SH, SR$_4$, or SO$_2$R$_4$; A is —NHCO—, —N(CH$_3$)—CO—, —NHCH$_2$—, —N(CH$_3$)—CH$_2$—, —NHSO$_2$—, —CH=CH—, —CH=CHF—, —COCH$_2$—, —CH$_2$CH$_2$—, —CH(OH)CH$_2$—, or —C≡C—;

$R_2$ is a hydrogen or a methyl or ethyl group;

$R_3$ is a hydrogen or a methyl or ethyl group;

n is 0, 1, 2, 3, 4, 5, or 6;

$R_1$ is selected from the group consisting of (a) $C_3$ to $C_8$ cycloalkyl; (b) H; (c) phenyl or substituted phenyl; (d) alkyl; (e) heterocyclic; and (f) bicyclic alkyl and $R_4$ is designated to mean that X is contained within a ring such as octahydroindole.

The pharmaceutically acceptable salts, and individual stereoisomers of compounds of structural formula (1.0) above, as well as mixtures thereof, are also contemplated as falling within the scope of the present invention.

This invention also provides pharmaceutical compositions comprising a pharmaceutically acceptable carrier in combination with an effective amount of a compound of formula (1.0).

The present invention also provides a method of treating conditions in which antagonism of histamine $H_3$ receptors may be of therapeutic importance such as allergy, inflammation, cardiovascular disease (i.e. hyper or hypotension), gastrointestinal disorders (acid secretion, motility) and CNS disorders involving attention or cognitive disorders, (i.e., Alzheimer's, Attention Deficit Disorder, age-related memory dysfunction, stroke, etc), psychiatric disorders (i.e., depression, schizophrenia, obsessive-compulsive disorders, etc.) and sleep disorders (i.e., narcolepsy, sleep apnea, isomnia, disturbed biological and circadian rhythms, hyper and hyposomnolence, and related sleep disorders), epilepsy, hypothalamic dysfunction (i.e., eating disorders such as obesity, anorexia/bulimia, thermoregulation, hormone release) comprising administering an effective amount of a compound of formula (1.0) to a patient in need of such treatment.

DETAILED DESCRIPTION OF THE INVENTION

Preferably for compounds of formula (1.0); $R_2$ and $R_3$ are H, methyl, or ethyl; the cyclopropane attended at the 4(5)-position of the imidazole ring has the trans configuration and when X is H, A is —CH$_2$CH$_2$—, —COCH$_2$—, —CONH—, —CON(CH$_3$)—, —CH=CH—, —C≡C—, —CH$_2$—NH—, —CH$_2$—N(CH$_3$)—, —CH(OH)CH$_2$—, —NH—CH$_2$—, —N(CH$_3$)—CH$_2$—, —NHSO$_2$—, —CH$_2$O—, —CH$_2$S—, CH$_2$SO$_2$—, or —CH$_2$S(O)—;

$R_2$ is a hydrogen or a methyl or ethyl group;

$R_3$ is a hydrogen or a methyl or ethyl group;

n is 0, 1, 2, 3, 4, 5, or 6;

$R_1$ is selected from the group consisting of (a) $C_3$ to $C_8$ cycloalkyl; (b) H; (c) phenyl or substituted phenyl; (d) alkyl; (e) heterocyclic; and (f) bicyclic alkyl such as (adamantyl) and when X is NH$_2$, NH(CH$_3$) N(CH$_3$)$_2$, OH, OCH$_3$, NHR$_4$, OR$_4$, SH, SR$_4$, SO$_2$R$_4$; A is —NHCO—, —N(CH$_3$)—CO—, —NHCH$_2$—, —N(CH$_3$)—CH$_2$—, —NHSO$_2$—,—CH=CH—, —CH=CHF—, —COCH$_2$—, —CH$_2$CH$_2$—, —CH(OH)CH$_2$—, or —C≡C—;

$R_2$ is hydrogen or a methyl or ethyl group;

$R_3$ is a hydrogen or a methyl or ethyl group;

n is 0, 1, 2, 3, 4, 5, or 6;

$R_1$ is selected from the group consisting of (a) $C_3$ to $C_8$ cycloalkyl; (b) H; (c) phenyl or substituted phenyl; (d) alkyl; (e) heterocyclic; and (f) bicyclic alkyl such as (adamantyl); and $R_4$ is designated to mean that X is contained within a ring such as octahydroindole. More preferably, the present invention provides compounds of the general formula:

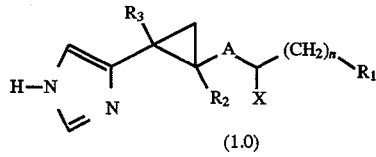

where A is —CONH— or —CH=CH—

X is H, NH$_2$ or NHR$_4$;

$R_2$ and $R_3$ are H;

n is 0, 1, 2 or 3;

$R_1$ is $C_6$ cycloalkyl or heterocyclic; and $R_4$ is designated to mean that X is contained within a ring such as octahydroindole.

The pharmaceutically acceptable salts, and individual stereoisomers of compounds of structural formula (1.0)

above, as well as mixtures thereof, are also contemplated as falling within the scope of the present invention.

Particularly preferred compounds include N-(1-cyclohexylmethyl)-3-(1H-imidazol-4-yl)-2-cyclopropanamide, L-cyclohexylalanine amide of 3-(1H-imidazol-4-yl) 2-cyclopropylamine, L-octahydro-indolyl-2-carboxylic amide of 3-(1H-imidazol-4-yl) 2-cyclopropylamine, 1-[(1H-imidazol)-4-yl)]-2-cyclopropyl-6-cyclohexyl-cis-3-hexene, and 1-[(1H-imidazol-4-yl)]-2-cyclopropyl-6-cyclohexyl-trans-3-hexene.

Representative compounds of this invention include compounds of the formulae (2.0) through (57.0):

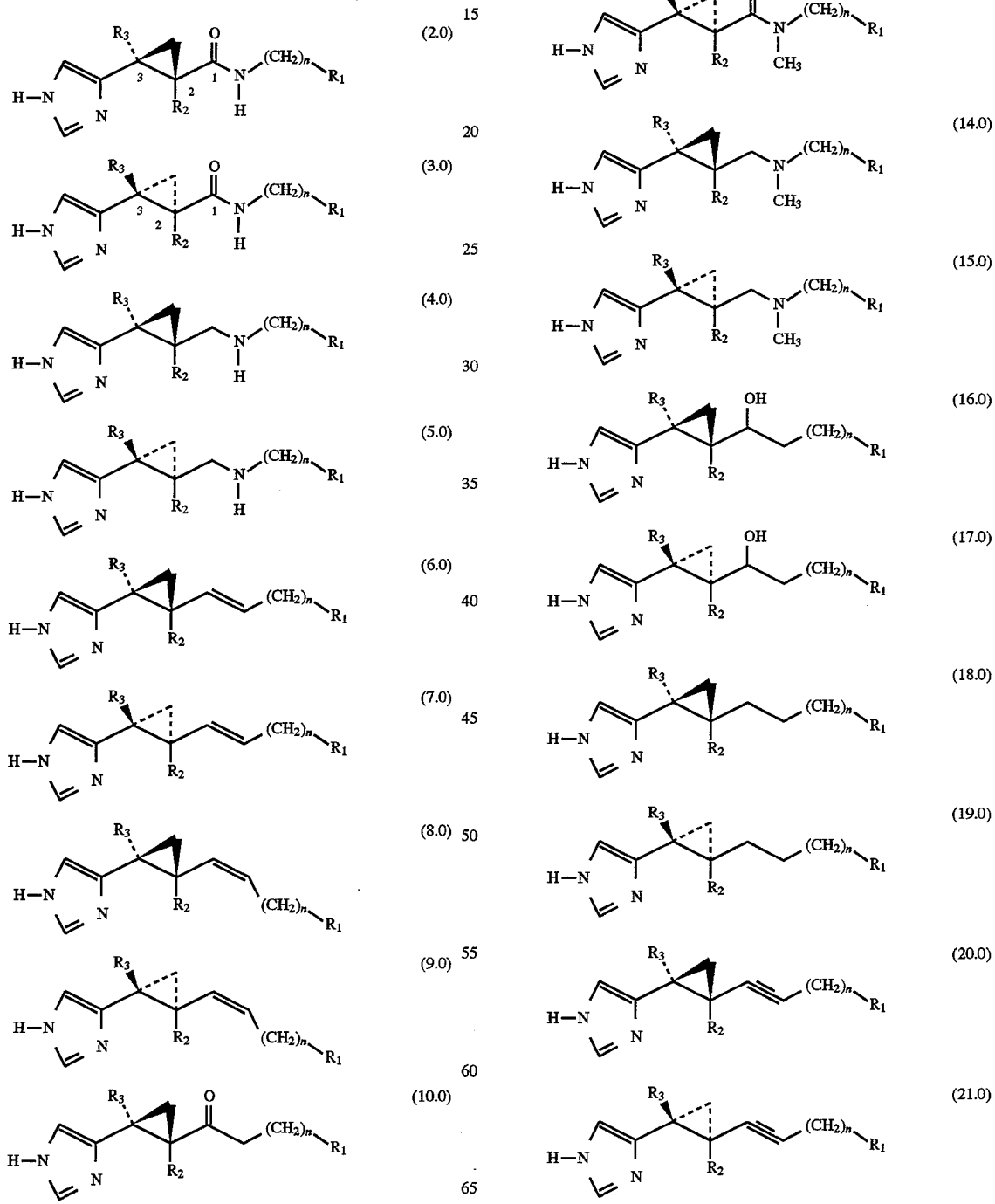

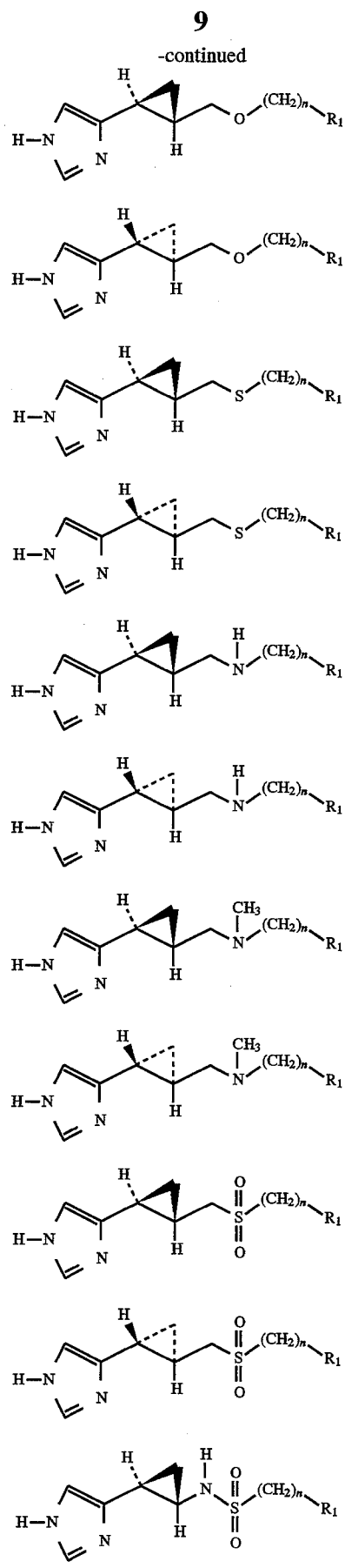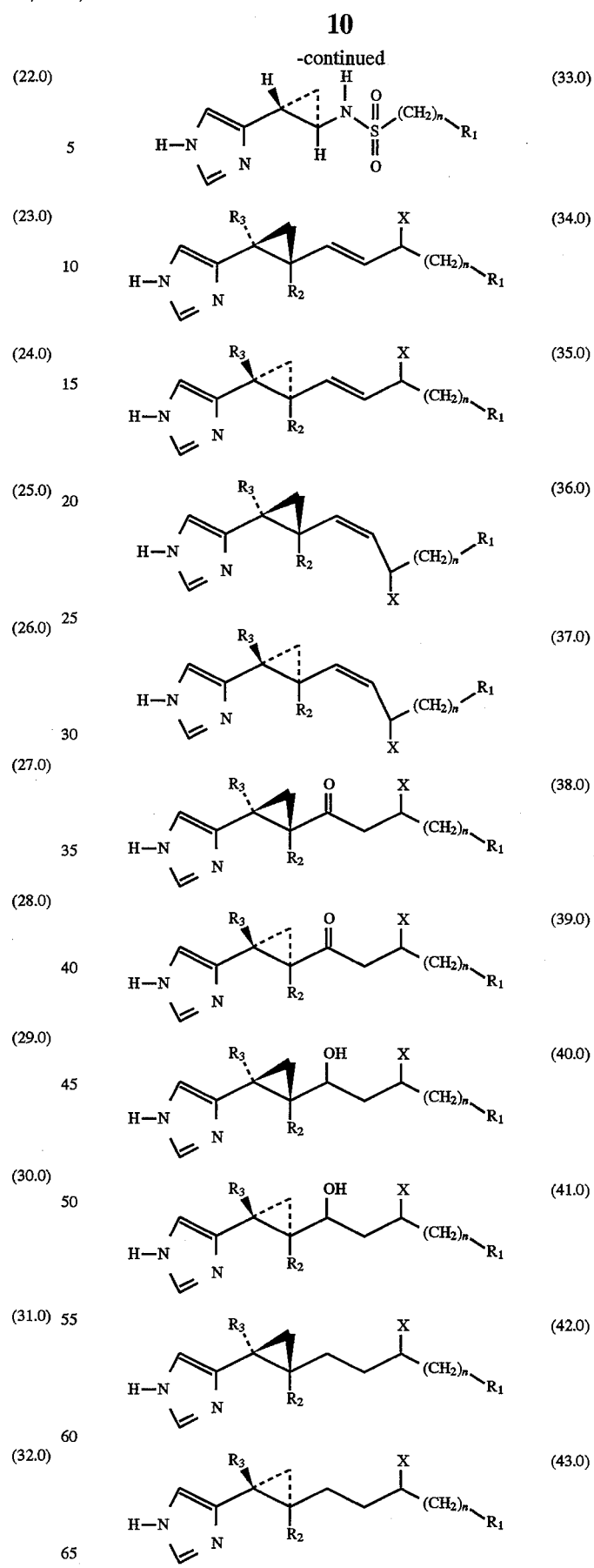

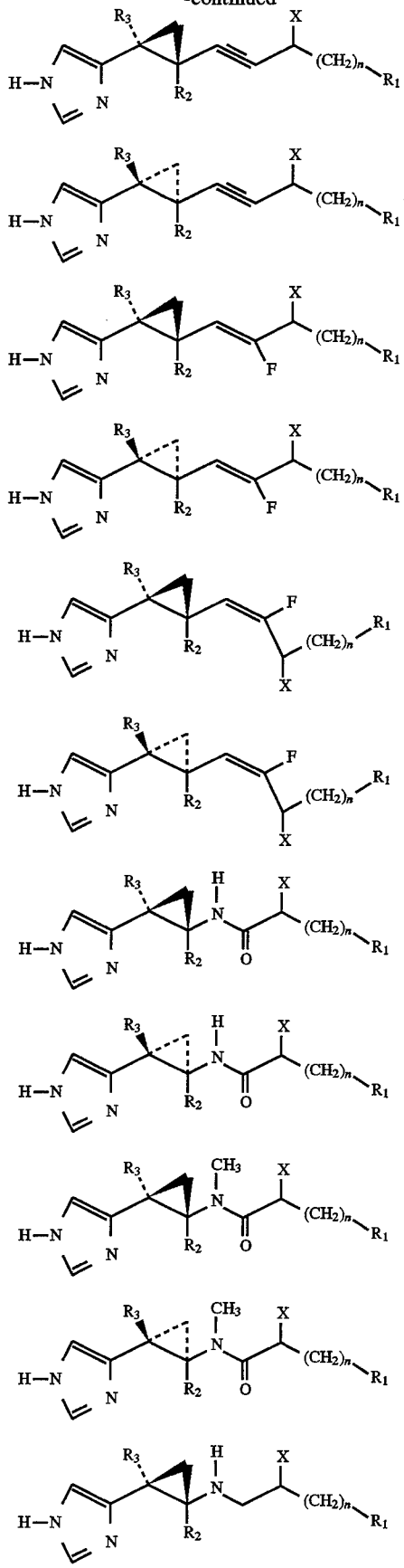

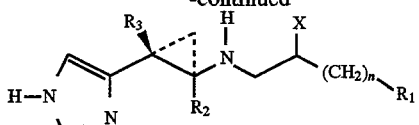

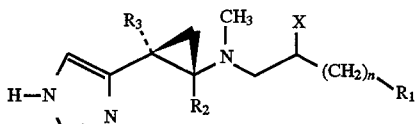

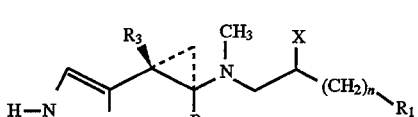

Certain compounds of the invention may exist in different isomeric (e.g., enantiomers and diastereoisomers) forms. The invention contemplates all such isomers both in pure form and in admixture, including racemic mixtures. Enol forms are also included.

The compounds of formula (1.0) can exist in unsolvated as well as solvated forms, including hydrated forms, e.g., hemi-hydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1–19 (1977) which is incorporated herein by reference.

As throughout this specification and appended claims, the following terms have the meanings ascribed to them:

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "heterocyclic" as used herein refers to a closed-ring structure in which one or more of the atoms in the ring is an element other than carbon. Representative heterocyclic groups are preferably saturated and include pyrrolidines, tetrahydrofuranes, tetrahydrothiophenes, tetrahydroisoquinolines and octahydroindole groups.

The term "substituted phenyl" as used herein refers to a phenyl group substituted by one or more groups such as alkyl, halogen, amino, methoxy, and cyano groups.

The term "bicyclic alkyl" as used herein refers to an organic compound having two ring structures connected to an alkyl group. They may or may not be the same type of ring and the rings may be substituted by one or more groups. Representative bicyclic alkyl groups include adamanthyl, decahydronaphthalene and norbornene.

Individual enantiomeric forms of compounds of the present invention can be separated from mixtures thereof by techniques well known in the art. For example, a mixture of diastereoisomeric salts may be formed by reacting the compounds of the present invention with an optically pure form of the acid, followed by purification of the mixture of diastereoisomers by recrystallization or chromatography and subsequent recovery of the resolved compound from the salt by basification. Alternatively, the optical isomers of the compounds of the present invention can be separated from one another by chromatographic techniques employing separation on an optically active chromatographic medium.

The present invention also provides pharmaceutical compositions which comprise one or more of the compounds of formula (1.0) above formulated together with one or more nontoxic pharmaceutically acceptable carriers. The pharmaceutical compositions may be specifically formulated for oral administration in solid or liquid form, parental injection, or for rectal administration.

The pharmaceutical compositions of this invention can be administered to humans and other animals orally, rectally, parenterally, intracisternally, lntravaginally, intraperitoneally, and topically in accordance with the present invention.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents and emulsifying agents.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as calcium stearate, magnesium stearate, solid polyethylene glycois, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredients(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum methydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976) p.33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of the invention.

The following processes and techniques may be employed to produce compounds of formula (1.0). The reactions are performed in a solvent appropriate to the reagents and materials employed and suitable for the transformation being effected. It is understood by those skilled in the art of organic synthesis that the functionality present in the molecule must be consistent with the chemical transformation proposed. This will frequently necessitate judgement as to the order of synthetic steps, protecting groups required and deprotection conditions.

A. PREPARATION OF COMPOUNDS WHEREIN A IS —CONH— OR CONCH$_3$—

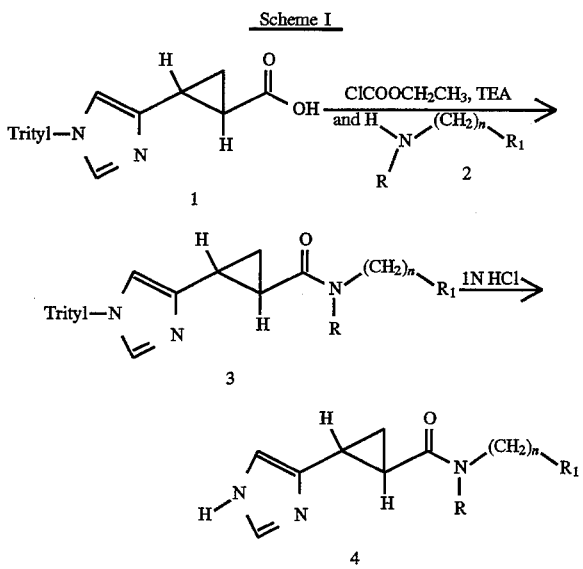

SCHEME I

According to the foregoing reaction scheme I, 3-[1-(Triphenylmethyl)-1H-imidazol-4-yl)]-2-cyclopropylcarboxylic acid (1), prepared as a racemic mixture of trans cyclopropanes using the method of Burger, et al., *J. Med. Chem.*, (1970), 13: 33–35, is converted to an activated ester through the action of ethyl chloroformate and triethylamine. The activated ester is reacted in situ with amine (2) to provide 3-[1-(Triphenylmethyl)-1H-imidazol-4-yl)]-2-cyclopropanecarboxamide (3). The Trityl protecting group can be removed with acid, preferably aqueous 1N HCl, to give 3-[1-(Triphenylmethyl)-1H-imidazol-4-yl]-2cyclopropanecarboxamide (4).

B. PREPARATION OF COMPOUNDS WHEREIN A IS —CH$_2$NH— OR —CH$_2$NCH$_3$—

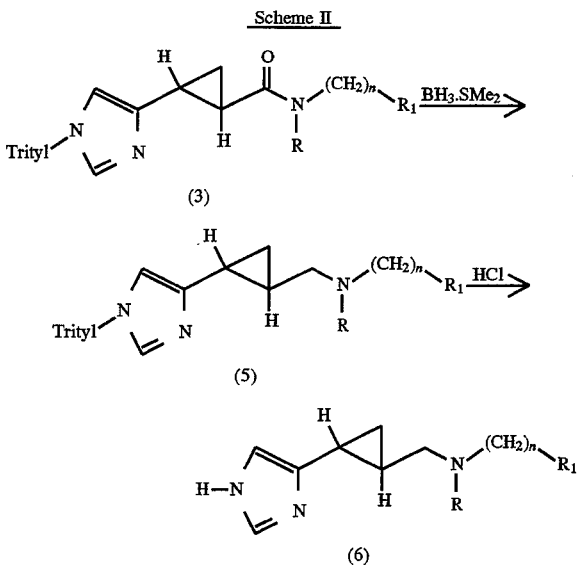

SCHEME II

According to the foregoing reaction scheme II, 3-[1-(Triphenylmethyl)-1H-imidazol-4-yl]2-cyclopropanecarboxamide (3), prepared as described in scheme I, is treated with excess borane-methyl sulfide complex to provide 3-[1-(Triphenylmethyl)-1H-imidazol-4yl]-2-cyclopropylamine (5). The Trityl protecting group is removed with aqueous HCl to give 3-(1H-imidazol-4yl)-2-cyclopropylamine (6).

C. PREPARATION OF COMPOUNDS WHEREIN A IS —CH(OH)CH$_2$— AND X IS H

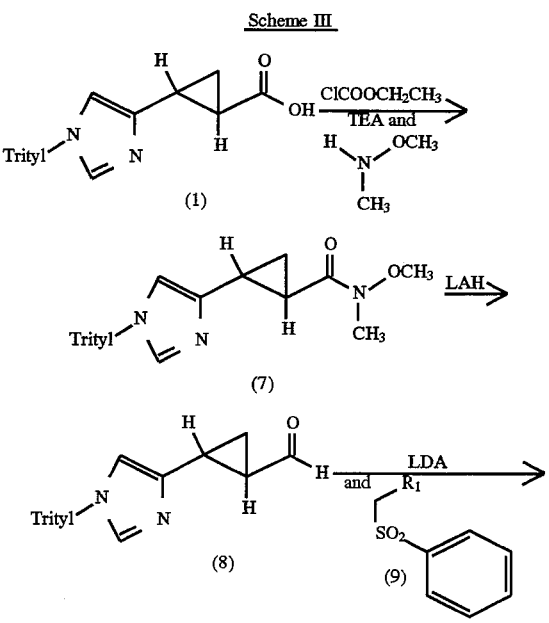

-continued

Scheme III

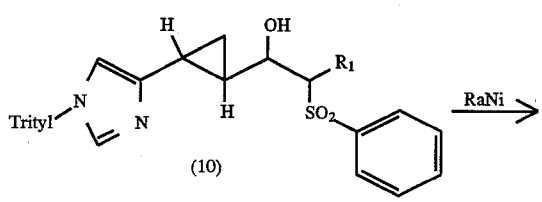

(10)

Raney nickel (W-2) at room temperature to give a mixture of alcohols (11). The Trityl protecting group can be removed, as previously described, to provide 3-(1H-imidazol-4-yl)-2-cyclopropyl alcohols (12).

D. PREPARATION OF COMPOUNDS WHEREIN A IS —CH=CH-(Trans Olefins)

Scheme IV

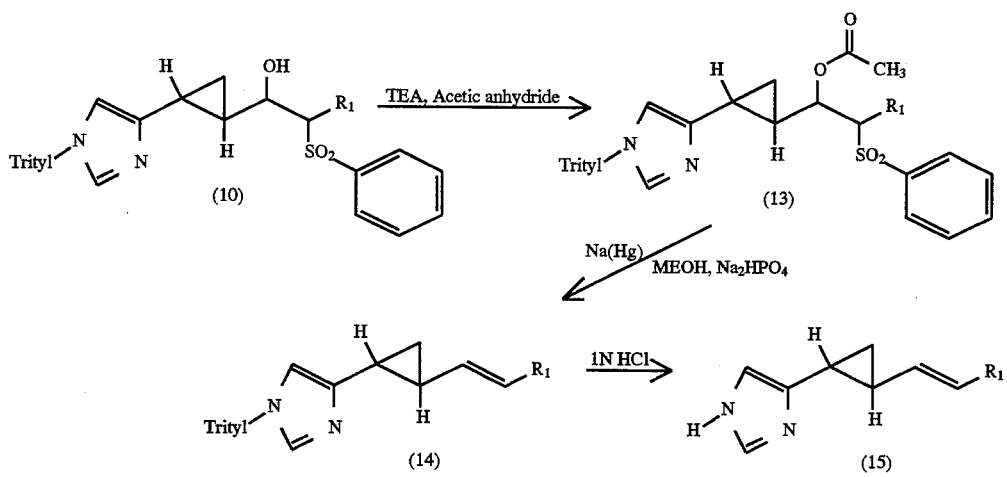

-continued
Scheme III

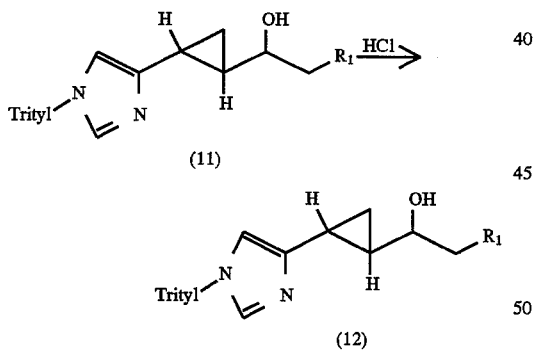

SCHEME IV

SCHEME III

According to the foregoing reaction scheme III, 3-[1-(Triphenylmethyl)-1H-imidazol-4-yl]-2-cyclopropanecarboxylic acid (1) is converted as in scheme I, to an activated ester through the action of ethyl chloroformate and triethylamine. The activated ester is reacted in situ with N,O-Dimethylhydroxylamine to form the Weinreb amide (7). Treatment of (7) with LAH at 0° C. gave 3-[1-(Triphenylmethyl)-1H-imidazol-4-yl]-2-cyclopropanecarboxaldehyde (8). The anion of sulphone (9) is prepared by the reaction of the sulphone with strong base, preferably LDA, and this anion is reacted with aldehyde (8), preferably at −78° C. The diastereoisomeric mixture of beta hydroxysulphones (10) produced, is treated with excess According to the foregoing reaction scheme IV, the diastereoisomeric mixture of beta hydroxy sulphones (10) synthesized as described in scheme III, is treated with acetic anhydride in the presence of triethylamine at room temperature to afford the corresponding mixture of beta acetoxy sulphones (13). This mixture is subsequently treated with excess 2–3% Na(Hg) in methanol in the presence of 4 equivalents of sodium hydrogen phosphate buffer to provide the 2-[1-(Triphenylmethyl-1H-imidazol-4-yl]-cyclopropyl trans olefin (14). Subsequent trityl deprotection gives 2-(1H-imidazol-4-yl)-cyclopropyl trans olefin (15).

E. PREPARATION OF COMPOUNDS WHEREIN A IS —CH=CH-(Cis olefins)

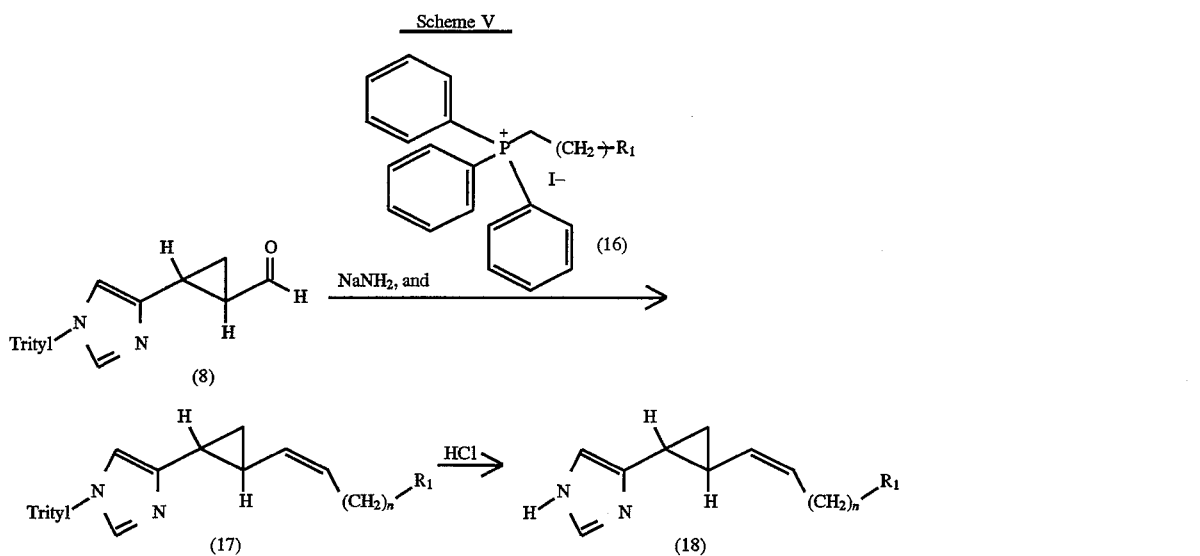

SCHEME V

According to the foregoing reaction scheme V, 3-[1-(Triphenylmethyl-1H-4-yl]-2-cyclopropyl carboxaldehyde (8) was convened to olefin (17) via treatment with the Wittig reagent derived from treatment of the phosphonium iodide salt (16) with strong base, preferably NaNH$_2$. As before, the Trityl protecting group was removed by treatment with aqueous 2N HCl to give 2-(1H-imidazol-4-yl)-cyclopropyl cis olefin (18).

F. PREPARATION OF COMPOUNDS WHEREIN A IS —COCH$_2$—

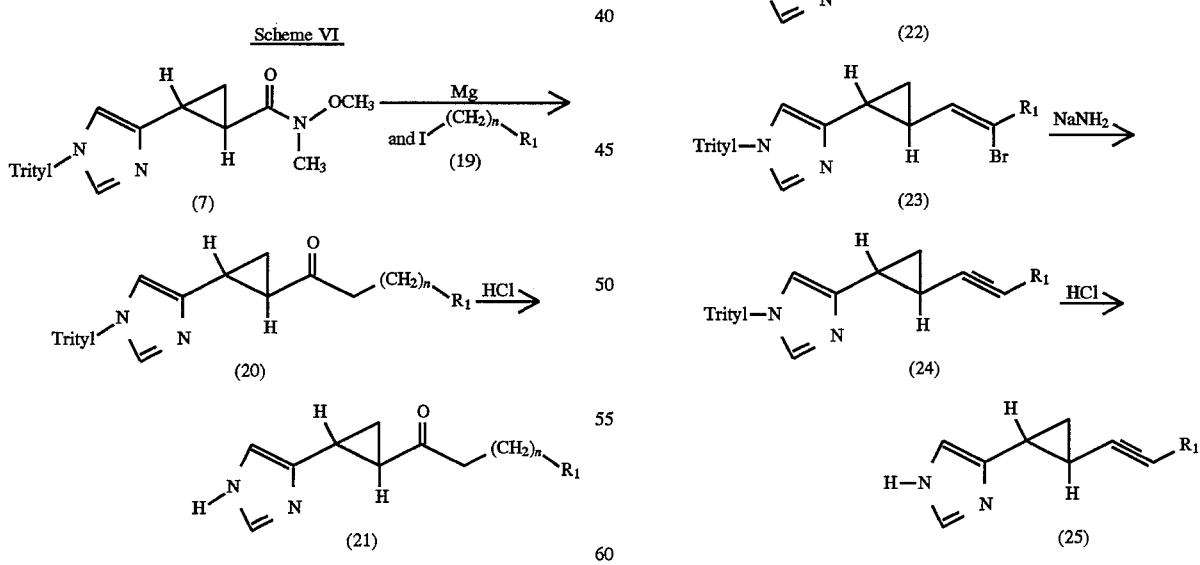

According to the foregoing reaction scheme VI, the Weinreb amide (7) is reacted with the Grignard reagent derived from treatment of iodide (19) with Magnesium metal, to provide 3-[1-(Triphenylmethyl)-1H-imidazol-4-yl]-2-cyclopropyl ketone (20). Trityl deprotection with HCl gives 3-[1H-imidazol-4-yl]-2-cyclopropyl ketone (21).

SCHEME VII

According to the foregoing reaction scheme VII, the 2-[1-(Triphenylmethyl)-1H-imidazol-4-yl]-cyclopropyl trans olefin (14), prepared following scheme IV, is reacted with bromine to give a mixture of vicinal dibromides (22).

Treatment of dibromides (22) with KOH provides 2-[1-(Triphenylmethyl)-1H-imidazol-4-yl]-cyclopropyl vinyl bromide (23). Subsequent reaction of the vinyl bromides (23) with base, preferably $NaNH_2$, affords 2-[1-(Triphenylmethyl)-1H-imidazol-4-yl]-cyclopropyl acetylenes (24). Finally, deprotection of the trityl protecting group with HCl gives 2-[1H-imidazol-4-yl]-cyclopropyl acetylenes (25).

H. PREPARATION OF COMPOUNDS WHEREIN A IS —$CH_2CH_2$—

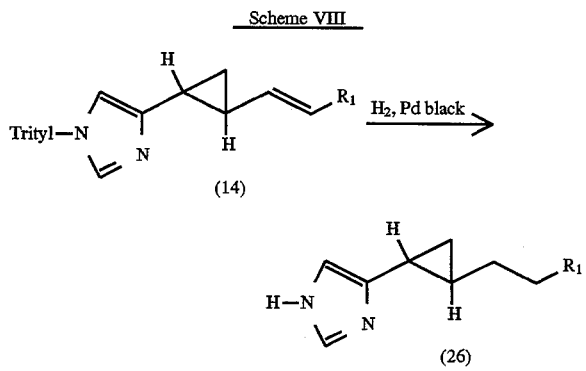

SCHEME VIII

According to the foregoing reaction scheme VIII, the 2-[1-(Triphenylmethyl)-1H-imidazol-4-yl]-cyclopropyl trans olefin (14), prepared following scheme IV, is subjected to catalytic hydrogenation under the conditions described by Zervas et al., *J. Am. Chem. Soc.*, 78: 1359 (1956), to reduce the carbon-carbon double bond and deprotect the trityl group, and provide the 2-(1H-imidazol-4-yl)-cyclopropane (26).

I. PREPARATION OF COMPOUNDS WHEREIN A IS —NHCO— OR —N(CH₃)CO— AND X IS $NH_2$

SCHEME IX

According to the foregoing reaction scheme IX, the racemic mixture of 2-[1-(Triphenylmethyl)-1H-imidazol-4-yl]-1(R)-2(S)-cyclopropylamine and 2-[1-(Triphenylmethyl)-1H-imidazol-4-yl]-1(S)-2(R)-cyclopropylamine (28), prepared according to the method of Burger et al., *J. Med. Chem.*, (1970), 13: 33–35, is reacted with the appropriate amino acid (27), (natural L-configuration), under standard peptide coupling conditions using DCC and HOBT. After the reaction is complete (tlc or hplc analysis), the diastereomeric mixture of amides (29) is separated by reverse phase HPLC chromatography using $CH_3CN/H_2O$/0.1% TFA as eluent to provide pure diastereoisomers (30) and (31).

J. PREPARATION OF COMPOUNDS WHEREIN A IS —$CH_2O$—

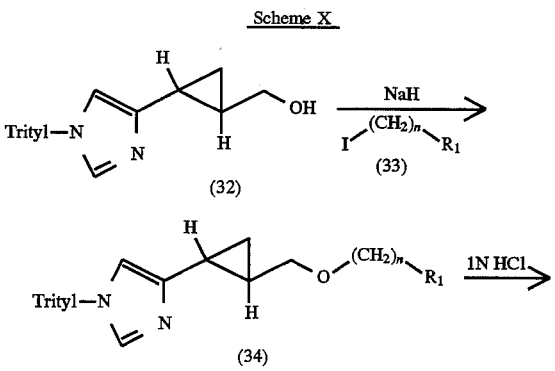

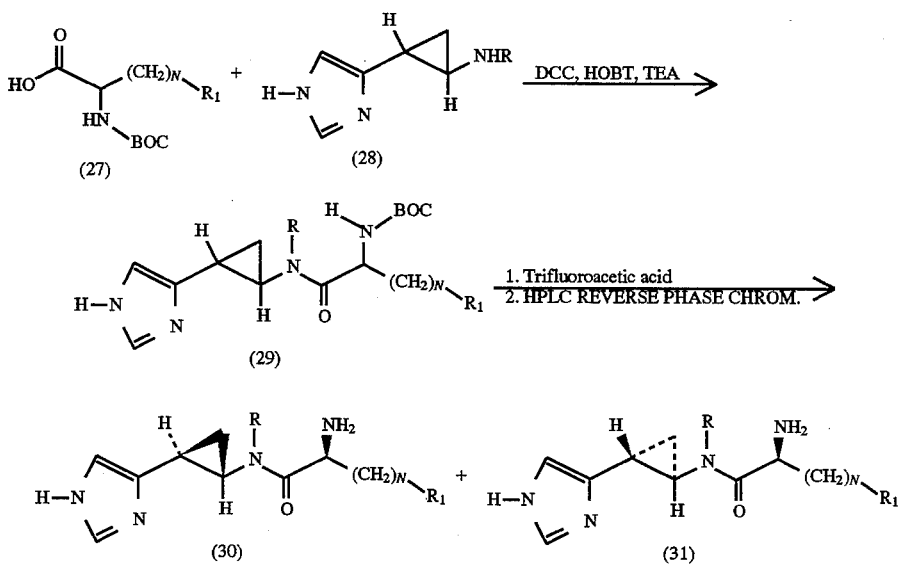

-continued
Scheme X

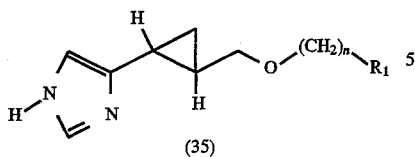
(35)

SCHEME X

According to the foregoing reaction scheme X, the racemic mixture of 3-[1-(Triphenylmethyl)-1H-imidazol-4-yl]-2-cyclopropyl alcohols (32) is treated with sodium hydride and reacted with iodide (33) to provide 3-[1-(Triphenylmethyl)-1H-imidazol-4-yl]-2-cyclopropyl ethers (34). The Trityl protecting group is removed with aqueous HCl to give 3-[1H-imidazol-4-yl]-2-cyclopropyl ether (35).

K. PREPARATION OF COMPOUNDS WHEREIN A IS —CH$_2$S—

Scheme XI

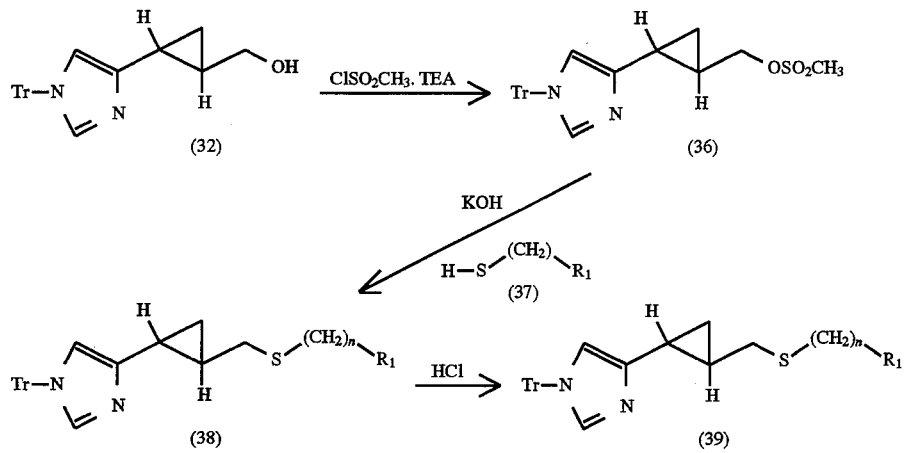

SCHEME XI

According to the foregoing reaction scheme XI, the racemic mixture of 3-[1-(Triphenylmethyl)-1H-imidazol-4yl]-2-cyclopropyl alcohol (32) is treated with methanesulfonyl chloride and triethylamine to provide the corresponding mesylates (36). The mesylates (36) were treated with thiolate (37) to afford 3-[1-(Triphenylmethyl)-1H-imidazol-4-yl]-2-cyclopropyl sulfides (38). The Trityl protecting group is removed with aqueous HCl to give 3-(1H-imidazol-4-yl)-2-cyclopropyl sulfides (39).

L. PREPARATION OF COMPOUNDS WHEREIN A IS —CH$_2$S(O)—

Scheme XII

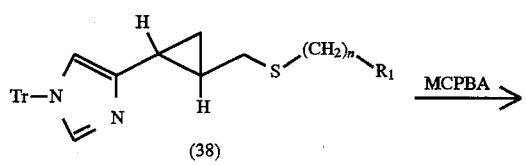

-continued
Scheme XII

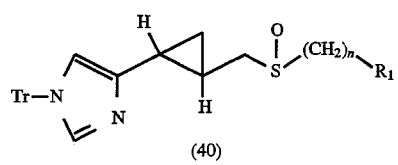
(40)

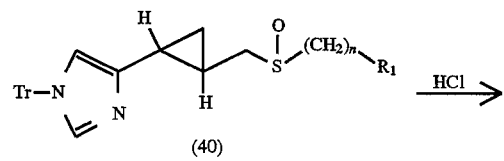

-continued
Scheme XII

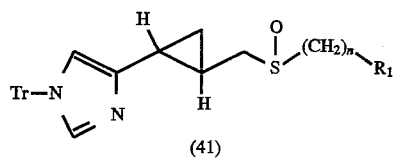
(41)

SCHEME XII

According to the foregoing reaction scheme XII, the racemic mixture of 3-[1-(Triphenylmethyl)-1H-imidazol-4-yl]-2-cyclopropyl sulfides (38) is treated with m-chloroperbenzoic acid to afford 3-[1-(Triphenylmethyl)-1H-imidazol-4-yl]-2-cyclopropyl sulfoxides (40). The Trityl protecting group is removed with aqueous HCl to give 3-[1H-imidazol-4-yl]-2-cyclopropyl sulfoxides (41) in accordance with scheme XIII.

M. PREPARATION OF COMPOUNDS WHEREIN A IS —CH$_2$SO$_2$—

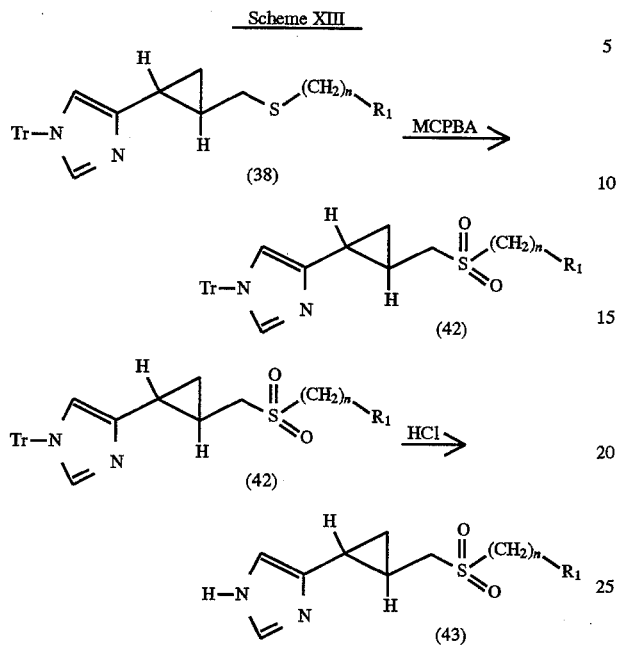

Scheme XIII

According to the foregoing reaction scheme XIII, the racemic mixture of 3-[1-(Triphenylmethyl)-1H-imidazol-4-yl]-2-cyclopropyl sulfides (38) is treated with two equivalents of m-chloroperbenzoic acid to afford 3-[1-(Triphenylmethyl)-1H-imidazol-4-yl]-2-cyclopropyl sulphones (42). The Trityl protecting group is removed with aqueous HCl to give 3-(1H-imidazol-4-yl)-2-cyclopropyl sulphones (43).

N. PREPARATION OF COMPOUNDS WHEREIN A IS —NHSO$_2$—

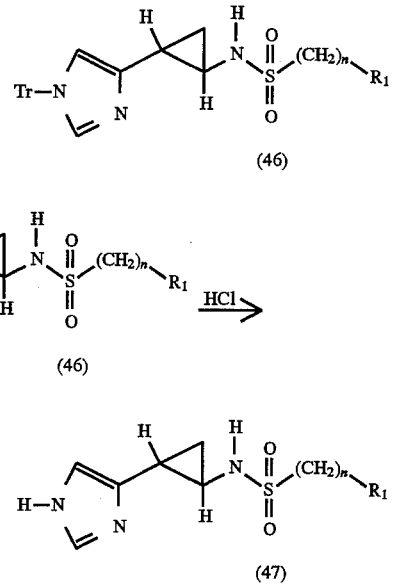

Scheme XIV

SCHEME XIV

According to the foregoing reaction scheme XIV, 2-[1-(Triphenylmethyl)-1H-imidazol-4-yl]-cyclopropylamine- (44), prepared as a racemic mixture of trans cyclopropanes using the method of Burger, et al., *J. Med. Chem.*, (1970), 13: 33–35, is treated with sulfonyl chloride (45) in the presence of triethylamine to afford the racemic mixture of 2-[1-(Triphenylmethyl)-1H-imidazol-4-yl]cyclopropyl sulfonamides (46). The trityl protecting group is removed with HCl to give 2-[1H-imidazol-4-yl]cyclopropyl sulfonamides (47).

O. PREPARATION OF CHIRAL CYCLOPROPANE COMPOUNDS

Scheme XV

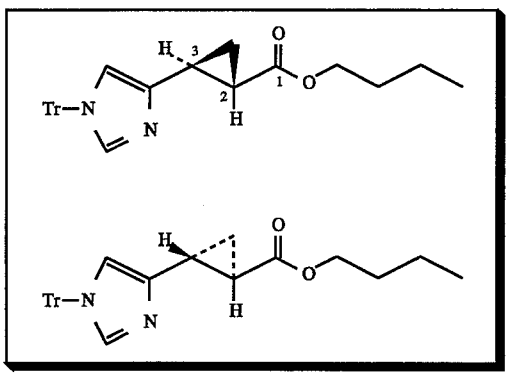
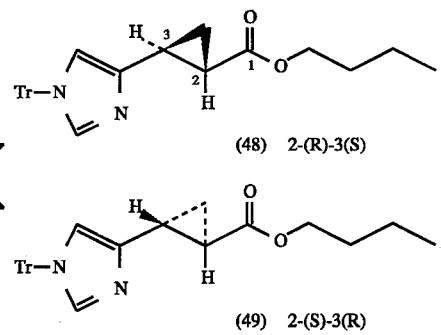

(48) 2-(R)-3(S)

(49) 2-(S)-3(R)

SCHEME XV

Chiral cyclopropane containing compounds that are claimed as histamine $H_3$ receptor antagonists were prepared from 3-[(1-(Triphenylmethyl-1H-imidazoyl-4-yl)]-2(R)-3(S)-cyclopropanoic butyl ester (48) or 3-[(1-Triphenylmethyl-1H-imidazoyl-4-yl)]-2(S)-3(R)-cyclopropanoic butyl ester (49). The racemic mixture of these enantiomers were separated using a chiral column (Regis serial #0112201) and a mobile phase of 90/10 Hexane/Isopropyl alcohol. Using this column, enantiomer (49) had a retention time of 7.315 minutes, and enantiomer (48) bad a retention time of 5.787 minutes.

The present invention is further illustrated by the following representative examples.

EXAMPLE 1

Preparation of racemic mixture of N-(1-Benzyl)-3-[(1H-imidazol-4-yl)]-2(R)-3(S)-cyclopropanamide and N-(1-Benzyl)-3-[(1H-imidazol-4-yl)]-2(S)-3(R)-cyclopropanamide hydrochloride

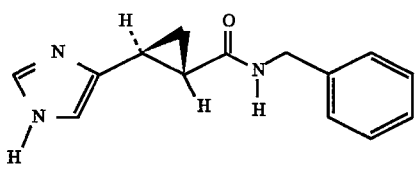

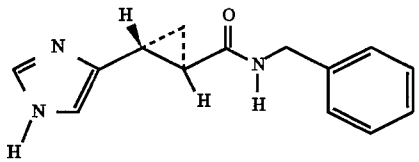

The racemic mixture of 3-[(1-Triphenylmethyl-1H-imidazoyl-4-yl)]-2(R)-3(S)-cyclopropanoic acid and 3-[(1-Triphenylmethyl-1H-imidazoyl-4-yl)]-2(S)-3(R)-cyclopropanoic acid, prepared according to the method of Burger, et al., *J. Med. Chem.*, (1970), 13: 33–35, (0.334 g, 0.84 mM) was suspended in 5 ml of distilled water. Sufficient acetone (35 ml) was added to complete solution, and the homogeneous solution was cooled to 0°–5° C. Triethylamine (0.101 g, 1.0 mM) in 5 ml of acetone was added, followed by dropwise addition of ethyl chloroformate (0.108 g, 1.0 mM). The reaction mixture was stirred for 30 minutes at 0° C., and then a solution of benzylamine (0.16 g, 1.5 mM) in 10 ml of acetone was added dropwise. The reaction mixture was stirred at 0°–5° C. for 1 hour, and then added to cold saturated ammonium chloride solution (100 ml), and extracted with ethyl acetate (2×100 ml). The combined ethyl acetate extracts were separated, dried over magnesium sulfate, filtered, and evaporated in vacuo to provide a crude yellow oil. The crude yellow oil was directly dissolved in 5 ml of methanol. 10 ml of 2N HCl was added, and the mixture heated at reflux for 40 minutes. The reaction mixture was cooled to room temperature, filtered, and the filtrate evaporated in vacuo to dryness. The remaining solid was triturated with a 1:1 mixture of ethyl acetate/hexanes (2×30 ml), collected by filtration, and dried under vacuum to give 109 mgs of a racemic mixture of N-(1-Benzyl)-3-[(1H-imidazol-4-yl)]-2(R)-3(S)-cyclopropanamide and N-(1-Benzyl)-3-[(1H-imidazol-4-yl)]-2(S)-3(R)-cyclopropanamide hydrochloride (47%).

NMR (CD$_3$OD), 300 MHz): d 7.74 (s, 1H), 7.30 (m, 5H), 6.92 (s, 1H), 4.37 (AB q, 2H), 2.35 (m, 1H), 1.88 (m, 1H), 1.42 (m, 1H), 1.24 (m, 1H). Mass Spectrum (DCl/NH$_3$): 242 (M+1)$^+$, MW=241.2942, C$_{14}$H$_{15}$N$_3$O$_1$.

EXAMPLE 2

Preparation of racemic mixture of N-(1-cyclohexylmethyl)-3-(1H-imidazol-4-yl)-2(R)-3(S)-cyclopropanamide and N-(1-cyclohexylmethyl)-3-(1H-imidazol-4-yl)-2(S)-3(R)-cyclopropanamide hydrochloride

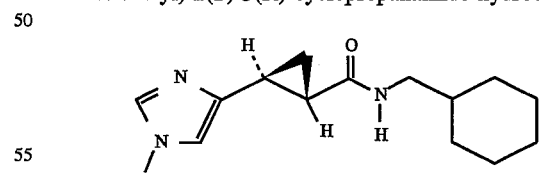

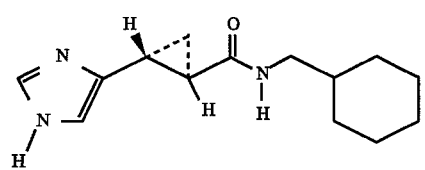

The racemic mixture of N-(1-cyclohexylmethyl)-3-(1H-imidazol-4-yl)-2(R)-3(S)-cyclopropanamide and N-(1-cyclohexylmethyl)-3-(1H-imidazol-4-yl)-2(S)-3(R)- cyclopropanamide hydrochloride was prepared as described in Example 1, except cyclohexanemethyl-amine was used instead of benzylamine.

NMR (CD₃OD, 300 MHz): d 7.78 (s, 1H), 6.92 (s, 1H), 3.02 (m, 2H), 2.30 (m, 1H), 1.84 (m, 1H), 1.74 (m, 4H), 1.45 (m, 1H), 1.35 (m, 1H), 1.22 (m, 3H), 0.94 (m, 2H).

Mass Spectrum (DCI/NH₃): 248 (M+1)⁺, MW=247.3422, $C_{14}H_{21}N_3O_1$.

EXAMPLE 3

Preparation of racemic mixture of N-[1-(3-Aminopropyl)-2-pipecoline]-3-(1H-imidazol-4-yl)-2(R)-3(S)-cyclopropanamide and N-[1-(3-Aminopropyl)-2-pipecoline]-3-(1H-imidazol-4-yl)-2(S)-3(R)-cyclopropanamide hydrochloride

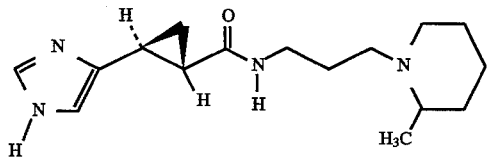

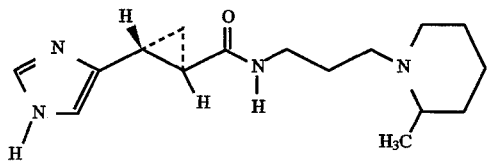

The racemic mixture of N-[1-(3-Aminopropyl)-2-pipecoline]-3-(1H-imidazol-4-yl)-2(R)-3(S)-cyclopropanamide and N-[1-(3-Aminopropyl)-2-pipecoline]-3-(1H-imidazol-4-yl)-2(S)-3(R)-cyclopropanamide hydrochloride was prepared as described in Example 1, except 1-(3-Aminopropyl)-2-pipecoline was used instead of benzylamine.

NMR (CD₃OD, 300 MHz): d 8.80 (s, 1H), 7.38 (s, 1H), 3.55 (m, 1H), 3.3 (m, 3H), 3.1 (m, 3H), 2.44 (m, 1H), 1.96 (m, 4H), 1.8 (m, 2H), 1.55 (m, 2H), 1.39 (d, 3H, J=6 Hz), 1.35 (m, 4H).

Mass Spectrum (DCI/NH₃): 291 (M+1)⁺, MW=290.4109, $C_{16}H_{26}N_4O_1$.

EXAMPLE 4

Preparation of racemic mixture of N-[4-(3-Aminopropyl) morpholine]-3-(1H-imidazol-4-yl)-2(R)-3(S)-cyclopropanamide and N-[4-(3-Aminopropyl)morpholine]-3-(1H-imidazol-4-yl)-2(S)-3(R)-cyclopropanamide hydrochloride

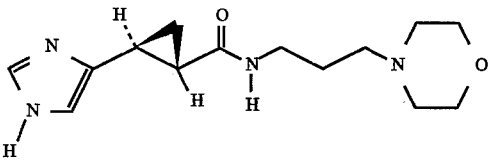

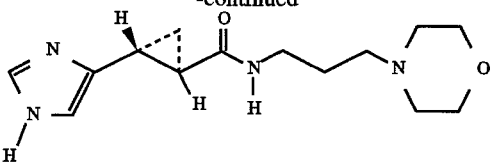

The racemic mixture of N-[4-(3-Aminopropyl) morpholine]-3-(1H-imidazol-4-yl)-2(R)-3(S)-cyclopropanamide and N-[4-(3-Aminopropyl)morpholine]-3-(1H-imidazol-4-yl)-2(S)-3(R)-cyclopropanamide hydrochloride was prepared as described in Example 1, except 4-(3-Aminopropyl)morpholine was used instead of benzylamine.

NMR (CD₃OD, 300 MHz): d 8.80 (s, 1H), 7.38 (s, 1H), 4.05 (m, 2H), 3.80 (m, 2H), 3.50 (m, 2H), 3.32 (m, 3H), 3.16 (m, 4H), 2.44 (m, 1H), 2.00 (m, 3H), 1.54 (m, 1H), 1.35 (m, 1H).

Mass Spectrum (DCI/NH₃): 279 (M+1)⁺, MW=278.3422, $C_{14}H_{22}N_4O_1$.

EXAMPLE 5

Preparation of racemic mixture of N-(phenyl)-3-(1H-imidazol-4-yl)-2(R)-3(S)-cyclopropanamide and N-(phenyl)-3-(1H-imidazol-4-yl)-2(S)-3(R)-cyclopropanamide hydrochloride.

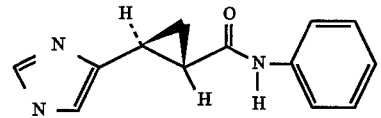

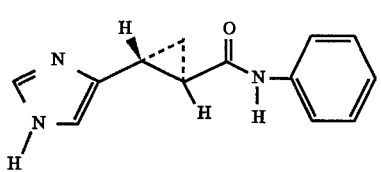

The racemic mixture of N-(phenyl)-3-(1H-imidazol-4-yl)-2(R)-3(S)-cyclopropanamide and N-(phenyl)-3-(1H-imidazol-4-yl)-2(S)-3(R)-cyclopropanamide hydrochloride was prepared as described in Example 1, except aniline was used instead of benzylamine.

NMR (CD₃OD, 300 MHz): d 7.56 (s, 1H), 7.53 (dd, 2H), 7.28 (m, 2H), 7.06 (m, 1H), 6.91 (s, 1H), 2.42 (m, 1H), 2.02 (m,1H), 1.48 (m, 1H), 1.33 (m, 1H).

Mass Spectrum (DCI/NH₃): 228 (M+1)⁺, MW=227.2672, $C_{13}H_{13}N_3O_1$.

EXAMPLE 6

Preparation of racemic mixture of N-[(R)-1-Cyclohexylethyl]-3-(1H-imidazol-4-yl)-2(R)-3(S)-cyclopropanamide and N-[(R)-1-Cyclohexylethyl]-3-(1H-imidazol-4-yl)-2(S)-3(R)-cyclopropanamide hydrochloride

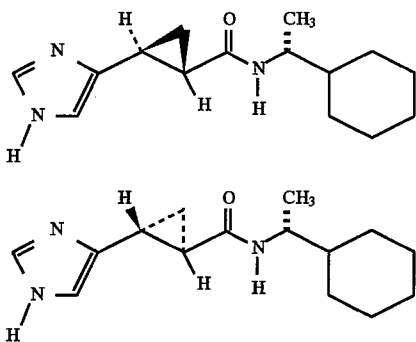

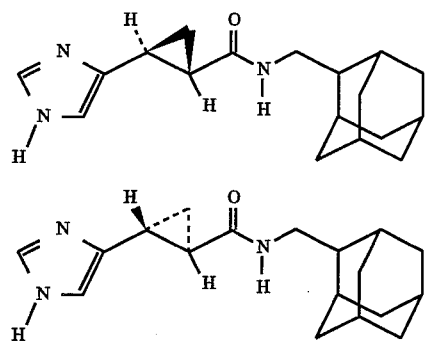

The racemic mixture of N-[(R)-1-Cyclohexylethyl]-3-(1H-imidazol-4-yl)-2(R)-3(S)-cyclopropanamide and N-[(R)-1-Cyclohexylethyl]-3-(1H-imidazol-4-yl)-2(S)-3(R)-cyclopropanamide hydrochloride was prepared as described in Example 1, except (R)-1-Cyclohexylethylamine was used instead of benzylamine.

NMR (CD$_3$OD, 300 MHz): d 8.78 (s, 1H), 7.36 (s, 1H), 3.73 (m, 1H), 2.41 (m, 1H), 1.97 (m,1H), 1.74 (m, 6H), 1.50 (m, 2H), 1.40–0.91 (m, 5H), 1.09 (d, 3H).

Mass Spectrum (DCl/NH$_3$); 262 (M+1)$^+$ MW=261.343; C$_{15}$H$_{23}$N$_3$O$_1$.

EXAMPLE 7

Preparation of racemic mixture of N-[(S)-1-Cyclohexylethyl]-3-(1H-imidazol-4-yl)-2(R)-3(S)-cyclopropanamide and N-[(S)-1-Cyclohexylethyl]-3-(1H-imidazol-4-yl)-2(S)-3(R)-cyclopropanamide hydrochloride

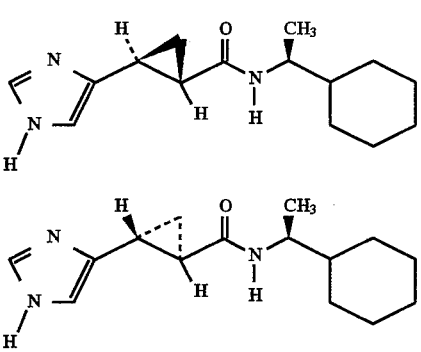

The racemic mixture of N-[(S)-1-Cyclohexylethyl]-3-(1H-imidazol-4-yl)-2(R)-3(S)-cyclopropanamide and N-[(S)-1-Cyclohexylethyl]-3-(1H-imidazol-4-yl)-2(S)-3(R)-cyclopropanamide hydrochloride was prepared as described in Example 1, except (S)-1-Cyclohexylethylamine was used instead of benzylamine.

NMR (CD$_3$OD, 300 MHz): d 8.78 (s, 1H), 7.36 (s, 1H), 3.73 (m, 1H), 2.41 (m, 1H), 1.97 (m,1H), 1.74 (m, 6H), 1.50 (m, 2H), 1.40–0.91 (m, 5H), 1.09 (d, 3H).

Mass Spectrum (DCl/NH$_3$): 262 (M+1)$^+$ MW=261.343, C$_{15}$H$_{23}$N$_3$O$_1$.

EXAMPLE 8

Preparation of racemic mixture of N-[1-Adamantylmethyl]-3-(1H-imidazol-4-yl)-2(S)-3(R)-cyclopropanamide hydrochloride and N-[1-Adamantylmethyl]-3-(1H-imidazol-4-yl)-2(R)-3(S)-cyclopropanamide.

The racemic mixture of N-[1-Adamantylmethyl]-3-(1H-imidazol-4-yl)-2(R)-3(S)-cyclopropanamide and N-[1-Adamantylmethyl]-3-(1H-imidazol-4-yl)-2(S)-3(R)-cyclopropanamide hydrochloride was prepared as described in Example 1, except 1-Adamantylmethylamine was used instead of benzylamine.

NMR (CD$_3$OD, 300 MHz): d 8.58 (s, 1H), 6.84 (s, 1H), 3.36 (m, 1H), 2.31 (m, 1H), 2.08–1.06 (m, 14H).

Mass Spectrum (DCl/NH$_3$): 300 (M+1)$^+$ MW=299.4181, C$_{18}$H$_{25}$N$_3$O$_1$.

EXAMPLE 9

Preparation of racemic mixture of N-[2-Phenylethyl]-3-(1H-imidazol-4-yl)-2(R)-3(S)-cyclopropanamide and N-[2-Phenylethyl]-3-(1H-imidazol-4-yl)-2(S)-3(R)-cyclopropanamide hydrochloride.

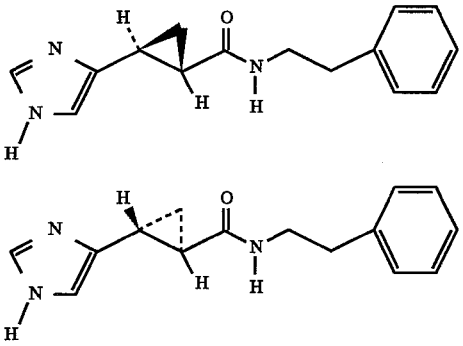

The racemic mixture of racemic mixture of N-[2-Phenylethyl]-3-(1H-imidazol-4-yl)-2(R)-3(S)-cyclopropanamide and N-[2-Phenylethyl]-3-(1H-imidazol-4-yl)-2(S)-3(R)-cyclopropanamide hydrochloride was prepared as described in Example 1, except 2-Phenylethylamine was used instead of benzylamine.

NMR (CD$_3$OD, 300 MHz): d 8.78 (s, 1H), 7.32 (s, 1H), 7.22 (m, 5H), 3.44 (t, 2H), 2.8 (t, 2H), 2.40 (m, 1H), 1.95 (m, 1H), 1.50 (m, 1H), 1.31 (m, 1H).

Mass spectrum (DCl/NH$_3$): 256 (M+1)$^+$ MW=255.3211, C$_{15}$H$_{17}$N$_3$O$_1$.

EXAMPLE 10

Preparation of racemic mixture of 3-(1-H-imidazol-4-yl)-2(S)-3(R)-cyclopropyl-3'-cyclohexylpropanone and 3-(1-H-imidazol-4-yl)-2(R)-3(S)-cyclopropyl-3'-cyclohexylpropanone.

Step 1.

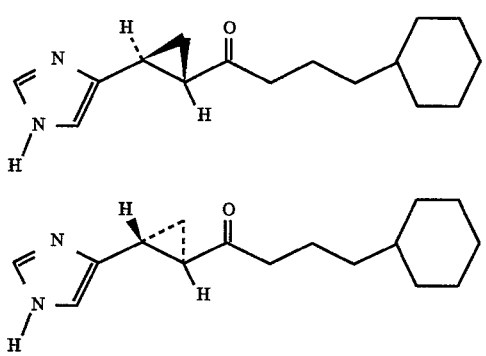

Racemic mixture of 3-(1-Triphenylmethyl-4-imidazoyl)-2 (S)-3(R)-cyclopropyl-3'-cyclohexylpropanone and 3-(1-H-imidazol-4-yl)-2(R)-3(S)-cyclopropyl-3'-cyclohexylpropanone.

To a 100 ml flask, placed under $N_2$, and charged with magnesium metal (0.076 g, 3.12 mM) and 3 ml of anhydrous ether, was aided dropwise (25 min), an ether solution (15 ml) of 3-cyclohexyl-propyl iodide (0.756 g, 3.0 mM). After 3 hours at room temperature the racemate of N,O-(Dimethyl) -3-(1-Triphenylmethyl-4-imidazoyl)-2(R)-3(S)-cyclopropanamide and N,O-(Dimethyl)-3-(1-Triphenylmethyl-4-imidazol-4yl)-2(S)-3(R)-cyclopropanamide (1.22 g, 2.8 mM) in 15 ml of anhydrous THF was added dropwise to the Grignard solution at 0° C. After 1 hour at 0° C., the reaction was warmed to 50° C., and kept at that temperature for 15 hours. The reaction mixture was cooled, and quenched by the addition of saturated ammonium chloride (100 ml), and extracted (2×100 ml) with ethyl acetate. The ethyl acetate extracts were combined, dried over magnesium sulfate, filtered, and evaporated in vacuo to give a crude yellow oil. The crude oil was purified using silica gel column chromatography (ethyl acetate: hexanes, 1:1) to provide 250 mgs of a racemic mixture of 3-(1-Triphenylmethyl)-1H-imidazol-4-yl)-2(S)-3(R)-cyclopropyl-3'-cyclohexylpropanone and 3-[1-(Triphenylmethyl)-1H-imidazol-4-yl]-2(R)-3(S)-cyclopropyl-3'-cyclohexylpropanone (18%).

NMR (CDCl$_3$, 300 MHz): d 7.3 (m, 12H), 7.10 (m, 4H), 6.72 (d, 1H), 2.38 (m, 3H), 1.8–1.6 (m, 2H), 1.5 (m, 9H), 1.20 (m, 7H).

Step 2.

The racemic mixture of 3(R)-[1-(Triphenylmethyl)-1H-imidazol-4-yl)]-2(S)-cyclopropyl-3'-cyclohexylpropanone and 3(S)-[1-(Triphenylmethyl)-1H-imidazol-4yl)-2(R)-cyclopropyl-3'-cyclohexylpropanone (0.250 g, 0.5 mM) was heated at reflux in 10 ml of 2N HCl and 2 ml of methanol for 40 minutes. The reaction mixture was cooled, filtered, and then neutralized to pH 7 with 5% sodium hydroxide solution, and extracted with chloroform (2×50 ml). The chloroform extracts were combined, dried over magnesium sulfate, filtered, and evaporated in vacuo to give a crude yellow oil. The crude oil was purified using preparative tlc with (CHCl$_3$: MeOH, 80:20) to afford 75 mgs of a racemic mixture of 3(R)-(1-H-imidazol-4yl)-2(S)-cyclopropyl-3' cyclohexylpropanone and 3(S)-(1-H-imidazol-4-yl)-2(R)-cyclopropyl-3'-cyclohexylpropanone (58%).

NMR (CD$_3$OD, 300 MHz): d 8.8 (d, 1H), 7.37(m, 1H), 2.47 (m, 2H), 2.14 (dt, 2H), 1.69 (m, 1H), 1.55 (m, 1H), 1.44 (m, 1H), 1.32–1.10 (m, 13H), 0.87 (m, 2H).

Mass Spectrum (DCI/NH$_3$); 261 (M+1)$^+$ MW=260.3814; $C_{16}H_{24}N_2O_1$.

EXAMPLE 11

Preparation of racemic mixture of N,N-(1-Methyl, 1-Cyclohexanemethyl)-3(S)-[(1H-imidazol-4-yl)]-2(R)-cyclopropanamide and N,N-(1-Methyl, 1-Cyclohexanemethyl)-3(R)-[1H-imidazol-4-yl)]-2(S)-cyclopropanamide.

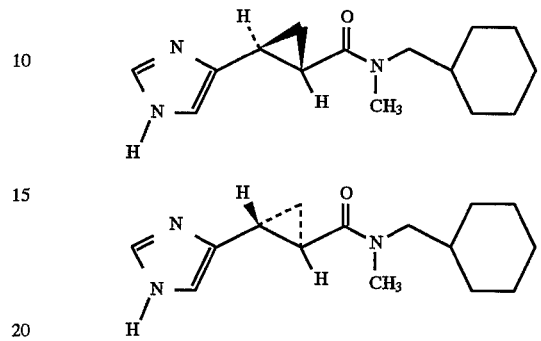

N,N-(1Methyl, 1-Cyclohexanemethyl)-3(S)-[(1H-imidazol-4-yl)]-2(R)-cyclopropanamide and N,N-(1-Methyl, 1-Cyclohexanemethyl)-3(R)-[(1H-imidazol-4-yl)]-2(S)-3(R)-cyclopropanamide was prepared as described in Example 1 except, N,N-(1-Methyl, 1-Cyclohexanemethyl) amine was used instead of benzylamine. The intermediate, N,N-(1-Methyl,1-Cyclohexanemethyl)-3(S)-[(1-Triphenylmethyl-1H-imidazol-4-yl)]-2(R)-cyclopropanamide and N,N-(1-Methyl, 1-Cyclohexanemethyl)-3(R)-[(1-Triphenylmethyl-1H-imidazol-4-yl)]-2(S)-cyclopropanamide was purified by silica gel column chromatography using (ethyl acetate:hexanes,4:6). The free base of N,N-(1-Methyl, 1-Cyclohexanemethyl)-3(S)-[(1H-imidazol-4-yl)]-2(R)-cyclopropanamide and N,N-(1-Methyl,1-Cyclohexanemethyl)-3(R)-[(1H-imidazol-4yl)]-2(S)-cyclopropanamide hydrochloride generated in the trityl deprotection step was made by neutralizing with 5% sodium hydroxide, extracting into CHCl$_3$, drying over magnesium sulfate, filtration, and evaporation in vacuo to provide a white foam.

NMR (CD$_3$OD, 300 MHz): d 7.78 (s, 1H), 6.92 (s, 1H), 3.02 (m, 2H), 2.30 (m, 1H), 2.20 (s, 3H),1.84 (m, 1H), 1.74 (m, 4H), 1.45 (m, 1H), 1.35 (m, 1H), 1.22 (m, 3H), 0.94 (m, 2H).

Mass Spectrum (DCI/NH$_3$): 262 (M+1)$^+$, MW=261.3692, $C_{15}H_{23}N_3O_1$.

EXAMPLE 12 AND 13

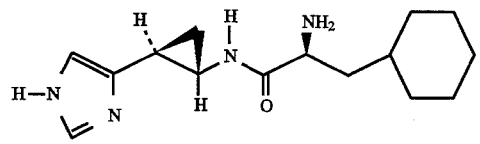

and

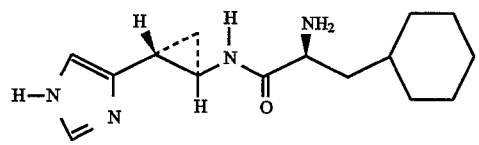

Preparation of the L-Cyclohexylalanine amide of 3(S)-(1H-imidazol-4-yl)-2(R)-cyclopropylamine and the the L-Cyclohexylalanine amide of 3(R)-(1H-imidazol-4yl)-2(S)-cyclopropylamine.

Boc-Cyclohexylalanine Dicyclohexylamine salt (0.497g, 1.1 mM) was added to a mixture of ethyl acetate (25 ml) and 0.5N HCl (25ml) for 30 minutes. The ethyl acetate layer was separated, washed with water (3×100 ml), dried over MgSO₄, and evaporated to give the Boc-Cyclohexylalanine free acid (1.1 mM). The acid was dissolved in 25 ml of THF and cooled to 5° C. under N₂. The acid was converted into a mixed anhydride by treatment with N-methyl morpholine (110 ul, 1 mM) and Isobutylchloroformate (130 ul, 1 mM). After stirring for 20 minutes, a solution of a racemic mixture of 3(S)-(1H-imidazol-4-yl)-2-(R)-cyclopropylamine and 3(R)-(1H-imidazol-4-yl)-2-(S)-cyclopropylamine (200 mgs, 1 mM) and triethylamine (284 ul, 2 mM) in 2 ml of water was added. After 2 hours, the reaction mixture was partioned between ethyl acetate (50 ml) and water (50 ml), the ethyl acetate layer was washed with saturated sodium bicarbonate solution, water, then dried over sodium sulfate, filtered, and evaporated in vacuo to give the BOC protected amine of L-Cyclohexylalanine amide of 3(S)-(1H-imidazol-4-yl)-2(R)-cyclopropylamine and its diastereoisomer the L-Cyclohexylalanine amide of 3(R)-(1-H-imidazol-4-yl)-2(S)-cyclopropylamine. The BOC group was deprotected by treating the crude amides directly with Trifluoroacetic add (5 ml) for 30 minutes at r.t. The TFA was evaporated, and the residue triturated with ether to provide the di-trifluoroacetic acid salt of the diastereoisomeric mixture of L-Cyclohexylalanine amide of 3(S)-(1-H-imidazol-4-yl)-2(R)-cyclopropylamine and the L-Cyclohexylalanine amide of 3(R)-(1H-imidazol-4-yl)-2(S)-cyclopropylamine (300 mgs).

The diastereoisomers were separated using reverse phase HPLC.

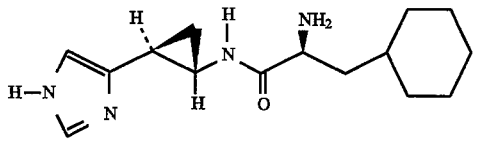

Di-Trifluoroacetic acid salt

NMR (D₂O, 300 MHz): d 8.44 (s, 1H), 7.18 (s, 1H), 3.88 (m, 1H), 2.87 (m, 1H), 2.09 (m, 1H), 1.6 (m, 6H), 1.27 (m, 2H), 1.1 (m, 5H), 0.88 (m, 2H).

Mass Spectrum (+FAB): [277 (M+1)⁺, 100%] MW=276.3839, C₁₅H₂₄N₄O₁.

Analytical HPLC: CH₃CN/H₂O/0.1% TFA; Gradient: 1 n, 0%, 25 ms, 25%, 30 ms, 100%; rt. 20.07 min.

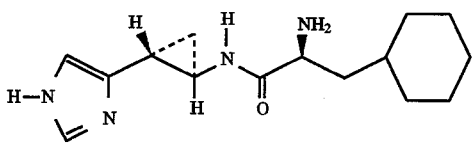

Di-Trifluoroacetic acid salt

NMR (D₂O, 300 MHz): d 8.44 (s, 1H), 7.18 (s, 1H), 3.88 (m, 1H), 2.87 (m, 1H), 2.06 (m, 1H), 1.6 (m, 6H), 1.27 (m, 2H), 1.1 (m, 5H), 0.88 (m, 2H).

Mass Spectrum (+FAB): [277 (M+1)⁺, 100%] MW=276.3839, C₁₅H₂₄N₄O₁.

Analytical HPLC: CH₃CN/H₂O/0.1% TFA; Gradient: 1 n, 0%, 25 ms, 25%, 30 ms, 100%; rt. 18.773 min.

EXAMPLE 14 AND 15

Preparation of the L-Octahydro-indolyl-2-carboxylic amide of 3(S)-(1H-imidazol-4-yl)-2(R)-cyclopropylamine and the L-Octahydro-indolyl-2-carboxylic amide of 3(R)-(1H-imidazol-4-yl)-2(S)-cyclopropylamine.

The preparation of the L-Octahydro-indolyl-2-carboxylic amide of 3(S)-(1H-5-imidazol-4-yl)-2(R)-cyclopropylamine and the the L-Octahydro-indolyl-2-carboxylic amide of 3(R)-1H-imidazol-4-yl)-2(S)-cyclopropylamine were prepared in the same way as examples 12 and 13 except L-Octahydro-indolyl-2-carboxylic acid was used instead of L-Cyclohexylalanine.

EXAMPLE 14

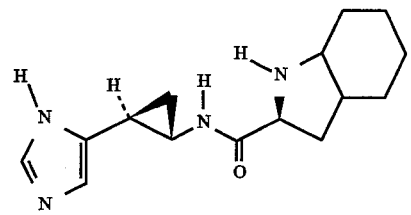

Di-Trifluoroacetic acid salt

NMR (D₂O, 300 MHz): d 8.4 (s, 1H), 7.06 (s, 1H), 4.25 (m, 1H), 3.65 (m, 1H), 2.8 (m, 1H), 2.30 (m, 2H), 2.2–0.90 (m, 12H).

Mass Spectrum (+FAB): [275 (M+1)⁺, 100%] MW=274.3678, C₁₅H₂₂N₄O₁.

Analytical HPLC: CH₃CN/H₂O/0.1% TFA; Gradient: 1 nn, 0%, 20 ms, 20%, 25 ms, 100%, 30 ms, 0%; rt. 14.54 min.

EXAMPLE 15

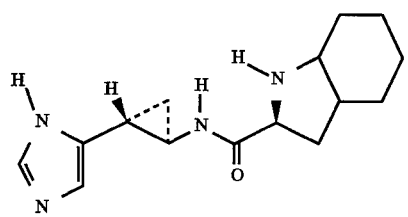

Di-Trifluoroacetic acid salt

NMR (D₂O, 300 MHz): d 8.4 (s, 1H), 7.06 (s, 1H), 4.25 (m, 1H), 3.65 (m, 1H), 2.8 (m, 1H), 2.30 (m, 2H), 2.1–1.0 (m, 12H).

Mass Spectrum (+FAB): [275 (M+1)⁺, 100%] MW=274.3678, C₁₅H₂₂N₄O₁.

Analytical HPLC: CH₃CN/H₂O/0.1% TFA; Gradient: 1 nn, 0%, 20 ms, 20%, 25 ms, 100%, 30 ms, 0%; rt. 16.03 min.

EXAMPLE 16

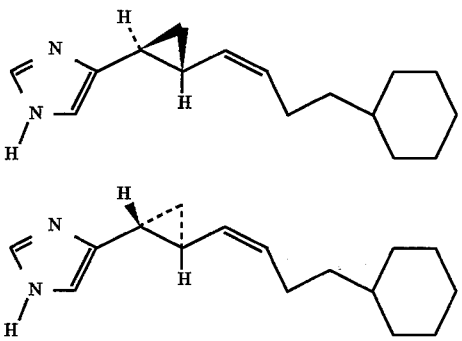

Step 1

Preparation of racemic mixture of 1(R)-[(1-Triphenylmethyl-1H-imidazol-4-yl)]-2(S)-cyclopropyl-6- cyclohexyl-cis-3-hexene and 1(S)-[(1-Triphenylmethyl-1H-imidazol-4-yl)]-2(R)-cyclopropyl-6-cyclohexyl-cis-3-hexene.

3-cyclohexylpropyl triphenylphosphonium iodide (1.36 g, 2.64 mM) was suspended in 100 ml of dry THF at r.t. under $N_2$. Sodium amide (0.102 g, 2.64 mM) was added, and the red-orange solution stirred for 1 hour at r.t. The solution containing the ylide derived from 3-cyclohexylpropyl triphenylphosphonium iodide was cooled to −78° C., and a THF solution (35 ml) of a racemic mixture of 3 (R)-[(1-Triphenylmethyl-1H-imidazol-4-yl)]-2(S)-cyclopropylcarboxaldehyde and 3(S)-[(1-Triphenylmethyl-1H-imidazol-4-yl)]-2(R)-cyclopropylcarboxaldehyde (1.0 g, 2.64 mM) was added slowly dropwise in 1 hour. After the addition of aldehyde was complete, the reaction was allowed to warm slowly to r.t. over a period of 5 hours. The reaction was quenched with saturated solution of ammonium chloride, and extracted with 2×150 ml of ethyl acetate. The ethyl acetate layer was separated, dried with magnesium sulfate, and evaporated in vacuo to afford the crude olefin. Purification using silica gel chromatography gave 327 mgs of racemic mixture of 1(R)-[(1-Triphenylmethyl-1H-imidazol-4-yl)]-2(S)-cyclopropyl-6-cyclohexyl-cis-3-hexene and 1(S)-[(1-Triphenylmethyl-1H-imidazol-4-yl)]-2(R)-cyclopropyl-6-cyclohexyl-cis-3-hexene.

NMR (CDCl$_3$, 300 MHz): d 7.34–7.08 (m, 15H), 6.96 (d, 1H), 6.55 (d, 1H), 5.30 (m, 1H), 4.84 (m, 1H), 2.14 (m, 1H), 2.00 (m, 1H), 1.93 (m, 1H), 1.78–0.76 (18H).

Mass Spectrum (DCl/NH$_3$): [488 (M+1)$^+$] MW=486.7024, $C_{35}H_{36}N_2$.

Step 2

The racemic mixture of 1(R)-[(1-Triphenylmethyl-1H-imidazol-4-yl)]-2(S)-cyclopropyl-6-cyclohexyl-cis-3-hexene and 1(S)-[(1-Triphenylmethyl-1H-imidazol-4-yl)]-2(R)-cyclopropyl-6-cyclohexyl-cis-3-hexene (0.320 g, 0.657 mM) was dissolved in 10 ml of 90% acetic acid/10% water. The reaction mixture was heated at 60° C. for 2 hours. The reaction mixture was cooled, added to 50 ml of 10% sodium hydroxide solution, and extracted with chloroform (2×50 ml). The chloroform extracts were combined, dried over MgSO$_4$, and evaporated in vacuo. Purification by silica gel chromatography gave 103 mgs (viscous yellow glass) of a racemic mixture of 1(R)-[(1H-imidazol-4-yl)]-2(S)-cyclopropyl-6-cyclohexyl-cis-3-hexene and 1(S)-[(1-H-imidazol-4-yl)]-2(R)-cyclopropyl-6-cyclohexyl-cis-3-hexene.

NMR (CD$_3$OD, 300 MHz): d 7.6 (s, 1H), 6.82 (s, 1H), 5.34 (m, 1H), 4.90 (m,1H), 2.18 (m, 2H), 1.90 (m, 3H), 1.60 (5H), 1.4–0.7 (m, 9H).

Mass Spectrum (DCl/NH$_3$): [245 (M+1)$^+$, 100%] MW=244.3814, $C_{16}H_{24}N_2$.

EXAMPLE 17

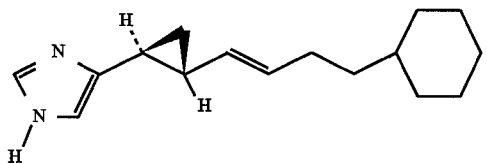

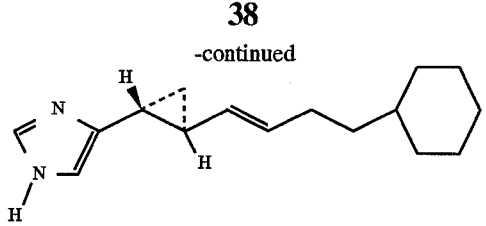

Preparation of racemic mixture of 1(R)-[(1H-imidazol-4-yl)]-2(S)-cyclopropyl-6-cyclohexyl-trans-3-hexene and 1(S)-[(1H-imidazol-4-yl)]-2(R)-cyclopropyl-6-cyclohexyl-trans-3-hexene.

Step 1

3-cyclohexylpropyl phenyl sulphone (1.1 g, 4.13 mM) was dissolved in 40 ml of dry THF and cooled to −78° C. under $N_2$. n-BuLi (1.65 ml, 4.13 mM) was added dropwise, and the solution stirred for 1 hour at −78° C. A THF solution (40 ml) of a racemic mixture of 3(R)-[(1-(Triphenylmethyl)-1H-imidazol-4-yl)]-2(S) cyclopropylcarboxaldehyde and 3(S)-[(1-(Triphenylmethyl)-1H-imidazol-4-yl)]-2(R)-cyclopropylcarboxaldehyde (1.56 g, 4.13 mM) was added dropwise in 15 minutes. After the addition of aldehyde was complete, the reaction was allowed to stir for 30 minutes, and then quenched with saturated ammonium chloride solution (200 ml). The reaction mixture was extracted with 2×150 ml of ethyl acetate. The ethyl acetate layer was separated, dried with magnesium sulfate, and evaporated in vacuo to afford the crude olefin. Purification using silica gel chromatography gave 1.01 g of racemic mixture of 1(R)-[(1-Triphenylmethyl-1H-imidazol-4-yl)]-2(S)-cyclopropyl-3-hydroxy-4-phenylsulphone-6-cyclohexyl-hexane and 1(S)-[(1-Triphenylmethyl-1H-imidazol-4-yl)]-2(R)-cyclopropyl-3-hydroxy-4-phenylsulphone-6-cyclohexyl-hexane.

NMR (CDCl$_3$, 300 MHz): d 7.92–7.5 (m, 5H), 7.34–7.04 (m, 15H), 6.6–6.46 (4 doublets, 2H),3.76 (m, 0.5H), 3.67 (m,0.5H), 3.14 (m, 0.5H), 3.02 (m, 0.5H), 2.2–0.6 (m, 19H).

Step 2

The racemic mixture of 1(R)-[(1-Triphenylmethyl-1H-imidazol-4-yl)]-2(S)-cyclopropyl-3-hydroxy-4-phenylsulphone-6-cyclohexyl-hexane and 1(S)-[(1-Triphenylmethyl-1H-imidazol-4-yl)]-2(R)-cyclopropyl-3-hydroxy-4-phenylsulphone-6-cyclohexyl-hexane (0.260 g, 0.40 mM) was dissolved in 20 ml of dry dichloromethane at r.t. under $N_2$. Triethylamine (0.116 ml, 0.80 mM) was added, followed by Acetic anhydride (0.047 ml). The reaction was stirred for 5 days at r.t., water was added, and the dichloromethane layer separated, dried with magnesium sulfate, filtered, and evaporated in vacuo. Purification using silica gel column chromatography and eluting with ethyl acetate/hexanes (3:7) gave 260 mgs of (white foam) racemic mixture of 1(R)-[(1-Triphenylmethyl-1H-imidazol-4-yl)]-2(S)-cyclopropyl-3-acetoxy-4-phenylsulphone-6-cyclohexyl-hexane and 1(S)-[(1-Triphenylmethyl-1H-imidazol-4-yl)]-2(R)-cyclopropyl-3-acetoxy-4-phenylsulphone-6-cyclohexyl-hexane.

NMR (CDCl$_3$, 300 MHz): d 7.92–7.5 (m, 5H), 7.34–7.04 (m, 15H), 6.6–6.46 (4 doublets, 2H),5.17 (m,0.5H), 5.04 (m, 0.5H), 3.76 (m, 0.5H), 3.02 (m, 0.5H), 2.2–0.6 (m, 19H), 2.1(s, 3H)CHN: $C_{43}H_{46}N_2S_1O_4$, MW=686.9144, Calc: C: 75.19, H: 6.75, N: 4.07; Found: C: 74.79, H: 6.89, N: 4.10

Step 3

The racemic mixture of 1(R)-[(1-Triphenylmethyl-1H-imidazol-4-yl)]-2(S)-cyclopropyl-3-acetoxy-4-phenylsulphone-6-cyclohexyl-hexane and 1(S)-[(1-Triphenylmethyl-1H-imidazol-4-yl)]-2(R)-cyclopropyl-3-acetoxy-4-phenylsulphone-6-cyclohexyl-hexane (0.103 g, 0.15 mM) was dissolved in 8 ml of dry methanol at 0° C. under N₂. Na₂HPO₄ (0.084 g, 0.60 mM) was added, followed by 3 g of 2% Na(Hg). The reaction mixture was stirred at 0°–5° C. for 2 hours, and then filtered through a pad of celite. The filtrate was evaporated, and the residue partioned between CHCl₃ and water. The CHCl₃ layer was separated, dried over MgSO₄, filtered, and evaporated in vacuo. Purification using tlc afforded 52 mgs of (viscous yellow glass) racemic mixture of 1(R)-[(1-Triphenylmethyl-1H-imidazol-4-yl)]-2(S)-cyclopropyl-6-cyclohexyl-trans-3-hexene and 1(S)-[(1-Triphenylmethyl-1H-imidazol-4-yl)]-2(R)-cyclopropyl-6-cyclohexyl-trans-3-hexene.

NMR (CDCl₃, 300 MHz): d 7.34–7.08 (m, 15H), 6.50 (d, 1H), 6.53 (d, 1H), 5.50 (m, 0.5H),5.30 (m, 0.5H),5.06 (m, 0.5H), 4.84 (m, 0.5H), 2.14 (m, 1H), 2.00 (m, 1H), 1.93 (m, 1H), 1.78–0.76 (18H).

Step 4

The racemic mixture of 1(R)-[(1-Triphenylmethyl-1H-imidazol-4-yl)]2(S)-cyclopropyl-6-cyclohexyl-trans-3-hexene and 1(S)-[(1-Triphenylmethyl-1H-imidazol-4-yl)]-2(R)-cyclopropyl-6-cyclohexyl-trans-3-hexene (0.052 g,0.106 mM) was heated at 80° C. in 1N HCl (6 ml) and ethanol (2 ml) for 30 minutes. The volatiles were removed by rotary evaporation, and the residue partioned between CHCl₃ (20 ml) and 10% NaOH solution. The CHCl₃ layer was separated, dried over MgSO₄, filtered, and evaporated in vacuo. Purification using tlc gave 17 mgs of a racemic mixture of 1(R)-[(1H-1H-imidazol-4-yl)]-2(S)-cyclopropyl-6-cyclohexyl-trans-3-hexene and 1(S)-[(1H-1H-imidazol-4-yl)]-2(R)-cyclopropyl-6-cyclohexyl-trans-3-hexene.

NMR (CDCl₃, 300 MHz): d 7.34–7.08 (m, 15H), 6.50 (d, 1H), 6.53 (d, 1H), 5.50 (m, 0.5H),5.30 (m, 0.5H), 5.06 (m, 0.5H), 4.84 (m, 0.5H), 2.14 (m, 1H), 2.00 (m, 1H), 1.93 (m, 1H), 1.78–0.76 (18H).

Mass Spectrum (DCl/NH₃): [245 (M+1)⁺, 100%] MW=244.3814, C₁₆H₂₄N₂.

EXAMPLE 18

Preparation of racemic 3(S)-(1H-1H-imidazol-4-yl)-2(R)-cyclopropyl-3'-cyclohexylpropyl ether and 3(R)-(1H-1H-imidazol-4-yl)-2(S)-cyclopropyl-3'-cyclohexylpropyl ether.

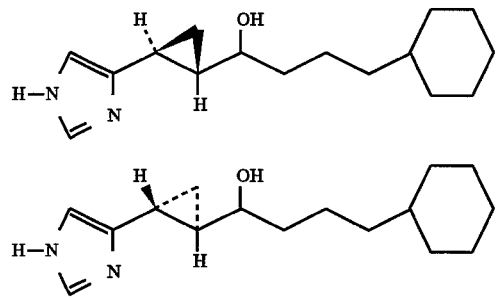

To a suspension of NaH (0.024 g, 1 mM) in 3 ml of dry DMF at 0° C. under N₂ was added a racemic mixture of 3(R)-(1-Triphenylmethy-1H-imidazol-4-yl)-2(S)-cyclopropanol and 3(S)-(1-Triphenylmethy-1H-imidazol-4-yl)-2(R)-cyclopropanol (0.190 g, 0.5 mM). After stirring for 30 minutes, 3-cyclohexylpropyl iodide (0.372 g, 1.5 mM) in 1 ml of DMF was added, and the reaction stirred at 0° C. for 20 minutes. The reaction was quenched with water (20 ml), and extracted with ethyl acetate (2×30 ml). The ethyl acetate layer was washed with brine, separated, dried over MgSO₄, filtered, and evaporated, in vacuo to afford 3-(R)-(1-Triphenymethyl-1H-imidazol-4-yl)-2(S)-cyclopropyl-3'-cyclohexylpropyl ether and 3-(S)-(1-Triphenymethyl-1H-imidazol-4-yl)-2(R)-cyclopropyl-3'-cyclohexylpropyl ether. The trityl group was deprotected directly by treatment with 2N HCl (10 ml) and heating at 80° C. for 30 minutes. The reaction mixture was cooled, filtered, and the filtrate evaporated in vacuo and triturated with ether to give 50 mgs of a racemic mixture of 3(S)-(1H-1H-imidazol-4-yl)-2(R)-cyclopropyl-3'-cyclohexylpropyl ether and 3(R)-(1H-1H-imidazol-4-yl)-2(S)-cyclopropyl-3'-cyclohexylpropyl ether.

NMR (CDCl₃, 300 Mhz): d: 8.00 (d,1H), 7.26 (d,1H), 3.60(m,3H), 1.72 (m,1H), 1.48 (m, 1H),1.58 (m, 11H), 1.24 (4H), 0.96 (m,1H), 0.75 (m, 1H).

Mass Spectrum: (DCl/NH₃)[M+1, 263, 100%)] MW=262.3974: C₁₆H₂₆O₁N₂

EXAMPLE 19

Preparation of racemic 1(S)-(1H-1H-imidazol-4-yl)-2(R)-cyclopropyl-3-hydroxy-6-cyclohexyl-hexane and 1(R)-(1H-1H-imidazol-4-yl)-2(S)-cyclopropyl-3-hydroxy-6-cyclohexyl-hexane.

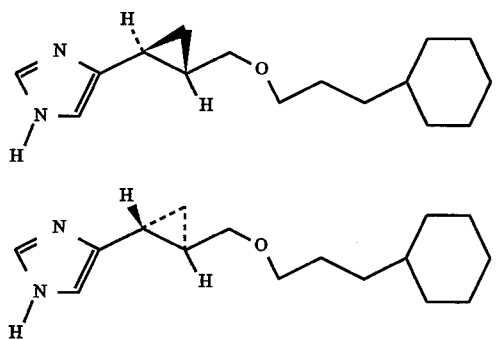

To a solution of a racemic mixture of 3-(1-Triphenylmethyl-1H-imidazol-4-yl)-2(S)-3(R)-cyclopropyl-3'-cyclohexylpropanone and 3-(1-Triphenylmethyl-1H-imidazol-4-yl)-2(R)-3(S)-cyclopropyl-3'-cyclohexylpropanone (251 mg, 0.5 mM) in 15 of methanol cooled to –20° C. was added portionwise NaBH₄ (185 mgs, 5 mM) in ten minutes. After 10 minutes, the reaction was quenched with KHSO₄ solution (5 ml). The reaction mixture was partioned between ethyl acetate and water (50/50). The ethyl acetate layer was separated, dried over MgSO₄, filtered, and evaporated in vacuo to give crude alcohols. The alcohols were added to 10 ml of 2N HCl and heated at 80° C. for 30 minutes. The reaction mixture was cooled, filtered, and the filtrate evaporated in vacuo, the triturated with ether to give 48 mgs of racemic 1(S)-(1H-1H-imidazol-4-yl)-2(R)-cyclopropyl-3-hydroxy-6-cyclohexyl-hexane and 1(R)-(1H-1H-imidazol-4-yl)-2(S)-cyclopropyl-3-hydroxy-6-cyclohexyl-hexane.

NMR (CD₃OD, 300 MHz): d 8.8 (d, 1H), 7.37(m, 1H), 2.07 (m, 2H), 1.74 (m, 2H), 1.69(m, 1H), 1.55 (m, 1H), 1.44 (m, 1H), 1.32–1.10 (m, 13H), 0.87 (m, 2H).

Mass Spectrum (DCl/NH₃); 263 (M+1)⁺ MW=262.3974; C₁₆H₂₆N₂O₁.

The compounds of this invention are antagonists of the histamine H₃ receptor. The binding affinity of the compounds of the invention to the H₃ receptor may be demonstrated by the procedure described below:

In Vitro Histamine H₃ Receptor Binding Analysis

Histamine H₃ receptor affinity was determined in rat cortical membranes using the H₃ selective agonist ligand,

[$^3$H]-N$^\alpha$-methylhistamine (78.9 Ci/mmole, DuPont NEN Research Products, Boston, Mass.) according to the method of West et al., (1990) *Mol. Pharmacol.* 38: 610–613 with modifications. Briefly, animals were sacrificed by decapitation and the cerebral cortex was rapidly removed. Rat cortices were mechanically homogenized with an Omni 1000 motor driven homogenizer in 10 volumes (wt/vol) of Krebs-Ringers Hepes buffer (pH 7.4) containing the following protease inhibitors; EDTA (10 mM), PMSF (0.1 mM), chymostatin (0.2 mg/50 mL) and leupeptin (0.2 mg/50 mL). The homogenate was centrifuged in a Sorvall at ~40,000× g for 30 min. The pellet was resuspended by mechanical homogenization in 25 mL water and lysed on ice for 30 min. The homogenate was recentrifuged and the membrane lysis was repeated. The membranes were recentrifuged and the final pellet was resuspended in 14 volumes of water to give approximately 200 µg protein/100 µl final concentration. The suspension was stored at −80° C. prior to use. Protein concentrations were determined by Coomassie Plus Protein Assay (Pierce, Rockford, Ill.).

The binding assay was carried out in polypropylene tubes in a total volume of 0.4 ml of 50 mM Na$^+$ Phosphate buffer (pH 7.4), containing 150–200 µg of tissue protein, 0.8–1.2 nM [$^3$H]-N$^\alpha$-methylhistamine and 0.3 to 10,000 nM GT-2016. Nonspecific binding (NSB) was accounted for by the inclusion of thioperamide (10 µM). Samples were incubated for 40 minutes at 25° C. The samples were filtered through glass fiber strips, pre-washed with 0.3% polyethyleneimine, using a Brandell cell harvester. The filters were rapidly washed three times with 4 ml of 25 mm Tris buffer containing 145 mM NaCl (pH 7.4, 4° C.). Filters were transferred to polyethylene minivials and counted in 3.5 ml of scintillation fluid (Ecolume, ICN Biomedicals, Inc.). Using this procedure, the non-specific binding was less than 10% of the total binding and the binding to the glass fiber filters was negligible. Saturation and competition experiments were analyzed with the ReceptorFit saturation and competition curve fittingprograms (Lundon Software, Inc., Cleveland, Ohio). $K_i$'s were determined using the equation $K_i=IC_{50}/(1+([Ligand]/[K_d])$. The results are given in Table 1.

TABLE 1

Histamine H₃ Receptor Binding Affinities

| Compound (nM) | Structure | | H₃ Receptor K$_i$ |
|---|---|---|---|
| Example 1 | 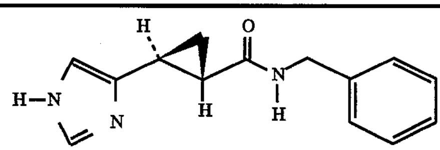 | | 53 ± 2 |
| Example 2 | 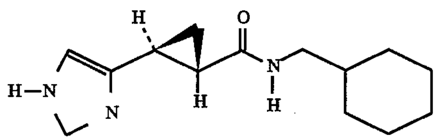 | | 37 ± 4 |
| Example 2a | 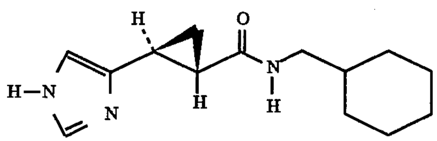 | | 23 ± 1 |
| Example 2b | 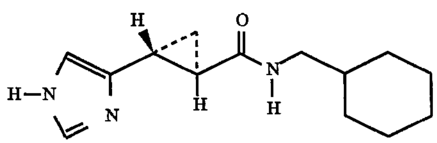 | | 176 ± 9 |
| Example 3 | 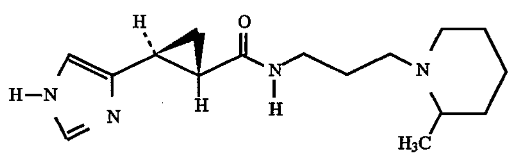 | | 659 ± 52 |
| Example 4 | 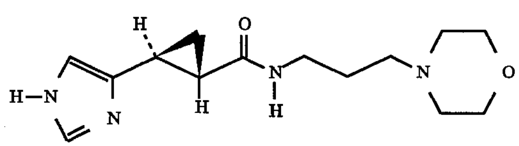 | | 1402 ± 158 |

TABLE 1-continued

Histamine H$_3$ Receptor Binding Affinities

| Compound (nM) | Structure | | H$_3$ Receptor K$_i$ |
|---|---|---|---|
| Example 5 | 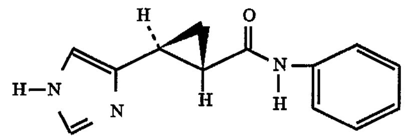 | | 267 ± 26 |
| Example 6 | 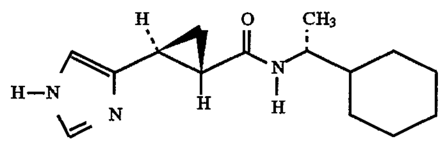 | | 70 ± 8.6 |
| Example 7 | 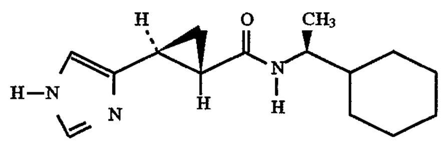 | | 146 ± 13 |
| Example 8 | 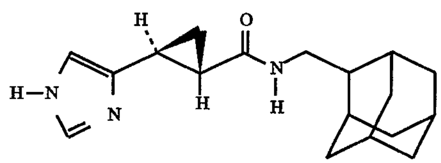 | | 55 ± 6 |
| Example 9 | 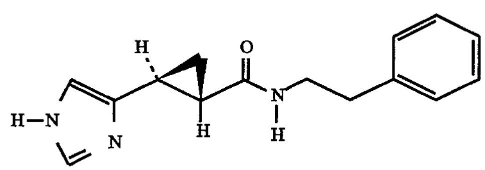 | | 163 ± 19 |
| Example 10 | 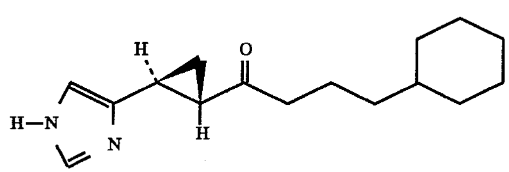 | | 97 ± 21 |

TABLE 1-continued

Histamine H$_3$ Receptor Binding Affinities

| Compound (nM) | Structure | H$_3$ Receptor K$_i$ |
|---|---|---|
| Example 11 | | 134 ± 13 |
| Example 12 | 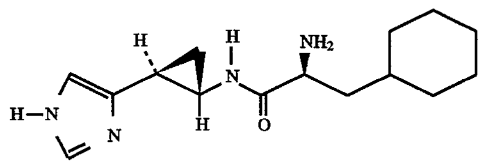 | 1.85 ± 0.5 |
| Example 13 | 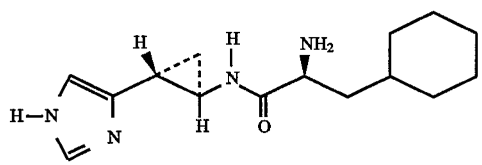 | 21.5 ± 1.8 |
| Example 14 | 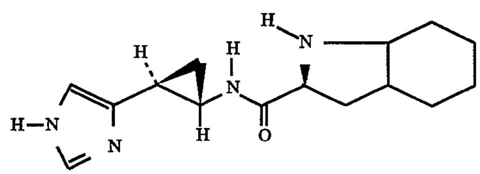 | 8.5 ± 0.7 |
| Example 15 | 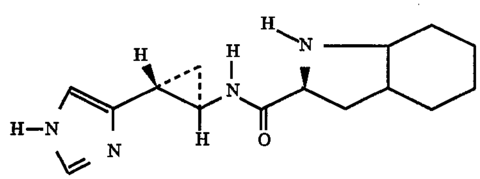 | 37 ± 4 |

TABLE 1-continued

Histamine H₃ Receptor Binding Affinities

| Compound (nM) | Structure | | H₃ Receptor $K_i$ |
|---|---|---|---|
| Example 16 | | | 12.2 ± 1.0 |
| Example 17 | | | 11.0 ± 1.0 |
| Example 18 | | | 240 ± 6.0 |
| Example 19 | | | 160 ± 9.0 |

What is claimed is:

1. A compound of the formula:

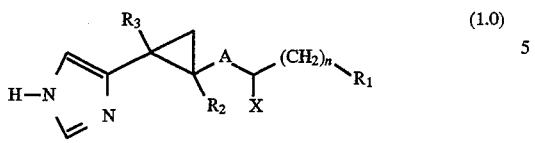
(1.0)

or a pharmaceutically acceptable salt or solvate thereof, wherein:

when X is H, A can be —$CH_2CH_2$—, —$COCH_2$—, —CONH—, —$CON(CH_3)$—, —CH=CH—, —C≡C—, —$CH_2$—NH—, —$CH_2$—$N(CH_3)$—, —$CH(OH)CH_2$—, —NH—$CH_2$—, —$N(CH_3)$—$CH_2$—, —$NHSO_2$—, —$CH_2O$—, $CH_2S$—, $CH_2SO_2$—, or —$CH_2S(O)$—;

$R_2$ is a hydrogen or a methyl or ethyl group;

$R_3$ is a hydrogen or a methyl or ethyl group;

n is 0, 1, 2, 3, 4, 5, or 6; and $R_1$ is selected from the group consisting of (a) $C_3$ to $C_8$ cycloalkyl; (b) H, (c) phenyl or substituted phenyl; (d) $C_1$ to $C_6$ alkyl; and (e) bicyclic alkyl having 5, 5 or 5, 6 ring structures;

when X is $NH_2$, $NH(CH_3)$, $N(CH_3)_2$, OH, $OCH_3$, or SH;

A is —NHCO—, —$N(CH_3)$—CO—, —$NHCH_2$—, —$N(CH_3)$—$CH_2$—, $NHSO_2$, —CH=CH—, —CH=CHF;

—$COCH_2$—, —$CH_2CH_2$—, —$CH(OH)CH_2$—, or —C≡C—;

$R_2$ is a hydrogen or a methyl or ethyl group;

$R_3$ is a hydrogen or a methyl or ethyl group;

n is 0, 1, 2, 3, 4, 5, or 6; and $R_1$ is selected from the group consisting of (a) $C_3$ to $C_8$ cycloalkyl; (b) H, (c) phenyl or substituted phenyl; (d) $C_1$ to $C_6$ alkyl; and (e) bicyclic alkyl having 5, 5 or 5, 6 ring structures.

2. A compound or a pharmaceutically acceptable salt or solvate thereof, as in claim 1 selected from the group consisting of:

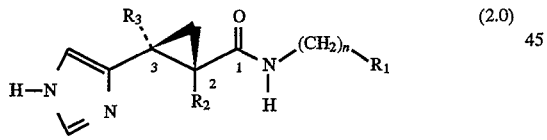
(2.0)

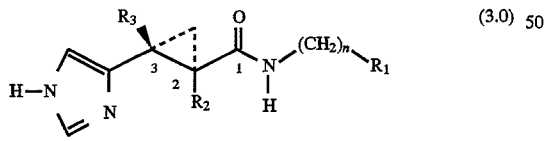
(3.0)

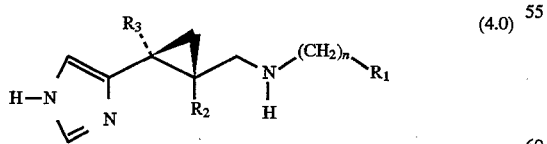
(4.0)

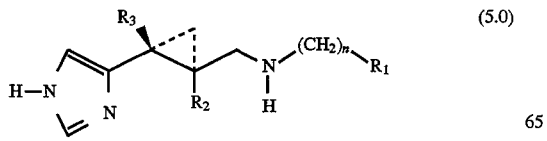
(5.0)

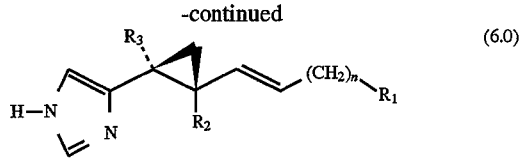
(6.0)

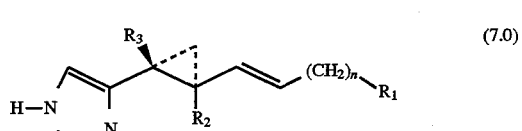
(7.0)

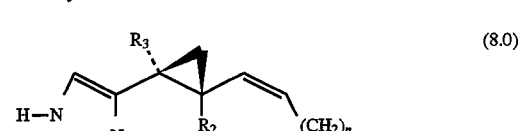
(8.0)

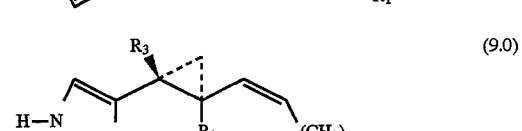
(9.0)

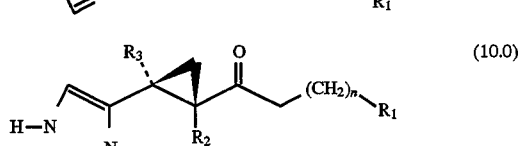
(10.0)

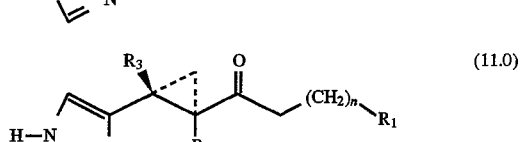
(11.0)

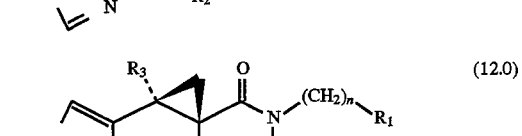
(12.0)

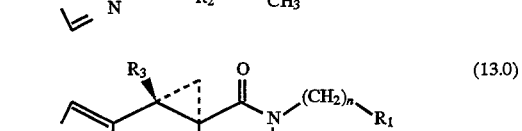
(13.0)

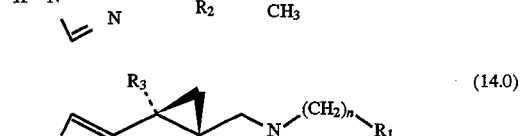
(14.0)

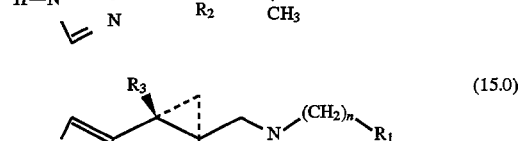
(15.0)

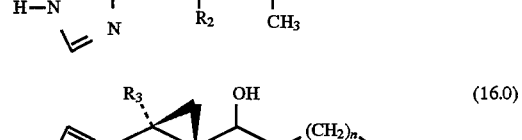
(16.0)

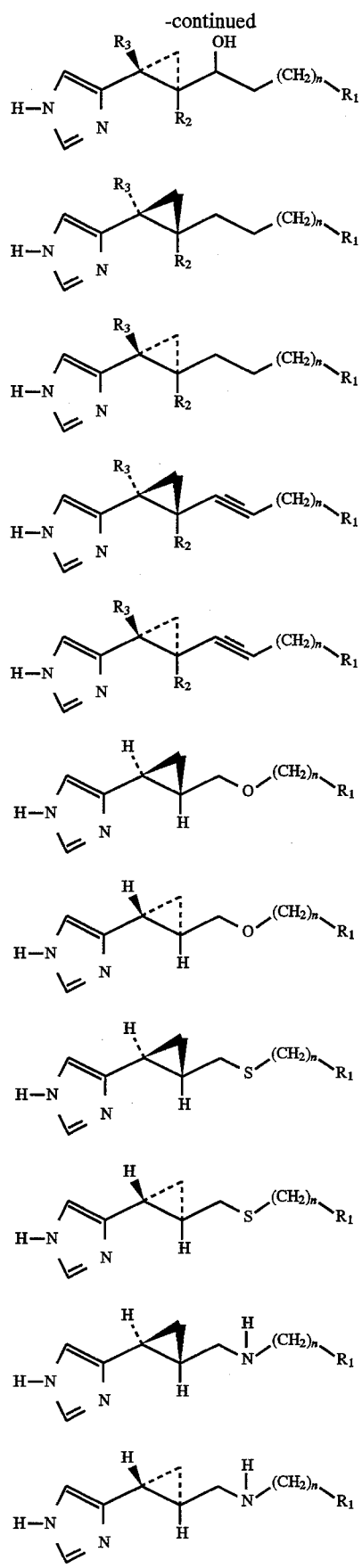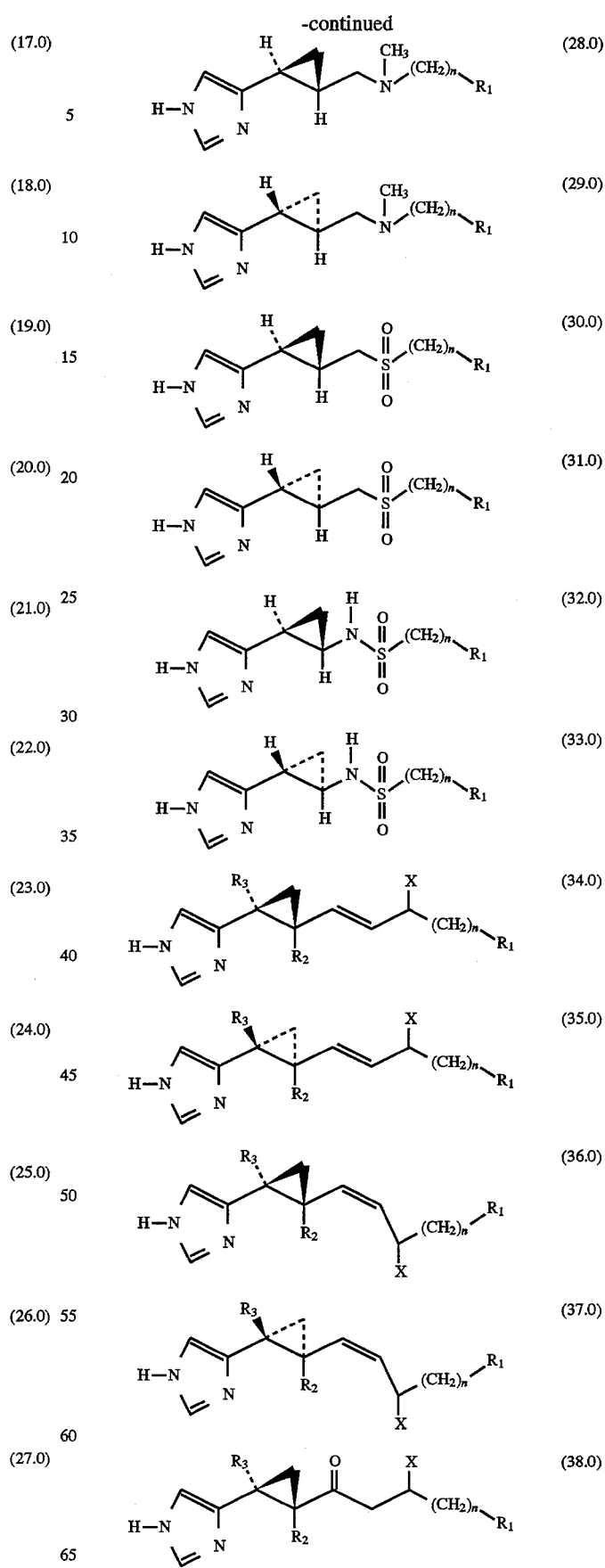

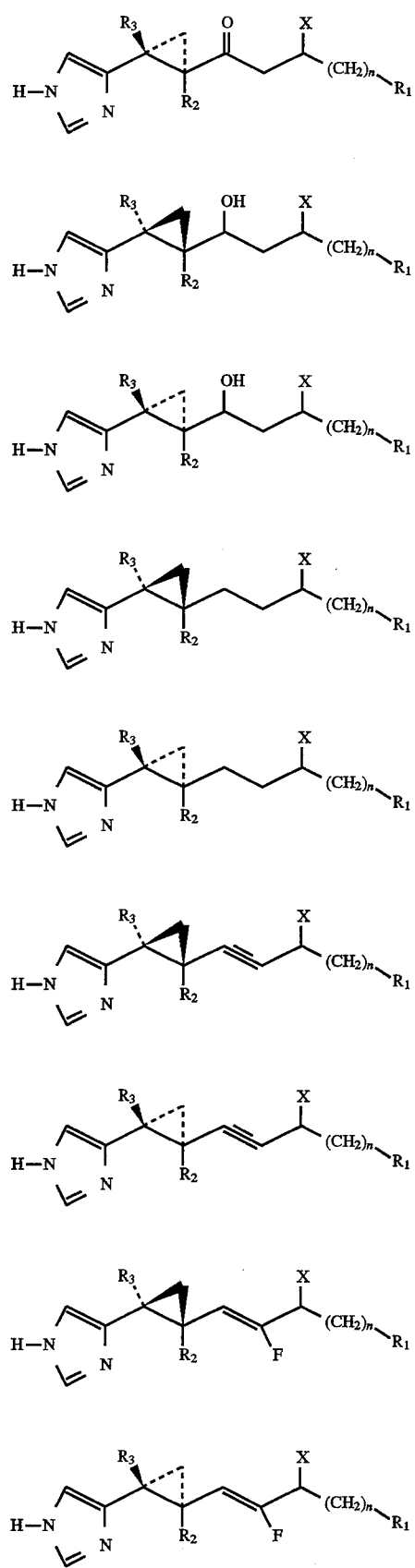
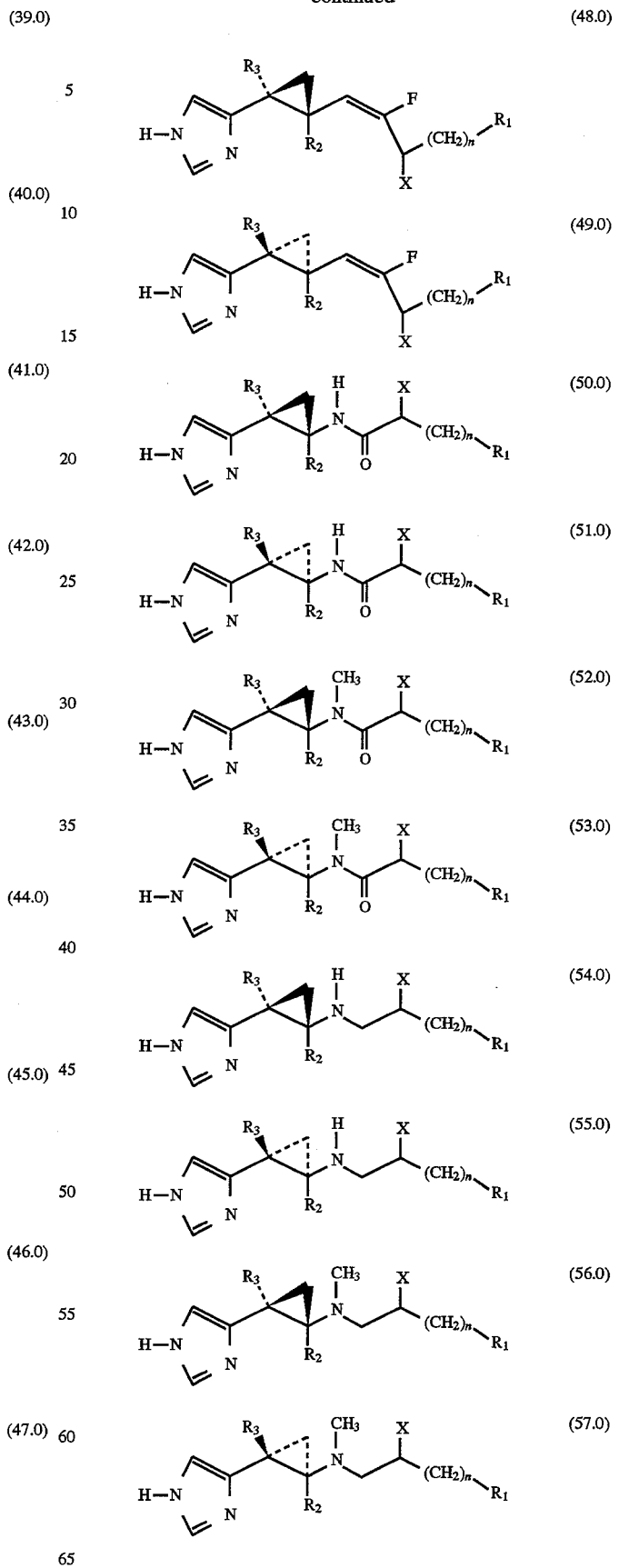
wherein $R_1$, $R_2$, $R_3$ X and n are as defined in claim 1.

3. A compound of the formula:
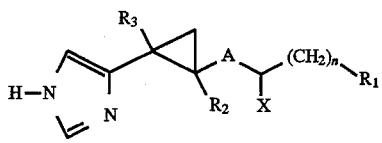
or a pharmaceutically acceptable salt or solvates thereof,
where A is —CONH— or —CH=CH—,
X is H, $NH_2$ or $NHR_4$;
$R_2$ and $R_3$ are H;
n is 0, 1, 2 or 3;
$R_1$ is $C_6$ cycloalkyl.
4. A pharmaceutical composition comprising an effective amount of at least one compound of claim 1 and a pharmaceutically acceptable carrier.
* * * * *